US006946688B2

(12) United States Patent
Grushin et al.

(10) Patent No.: US 6,946,688 B2
(45) Date of Patent: Sep. 20, 2005

(54) ELECTROLUMINESCENT IRIDIUM COMPOUNDS WITH FLUORINATED PHENYLPYRIDINES, PHENYLPYRIMIDINES, AND PHENYLQUINOLINES AND DEVICES MADE WITH SUCH COMPOUNDS

(75) Inventors: Vladimir Grushin, Hockessin, DE (US); Daniel David Lecloux, Buellton, CA (US); Viacheslav A. Petrov, Hockessin, DE (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 110 days.

(21) Appl. No.: 10/696,003

(22) Filed: Oct. 29, 2003

(65) Prior Publication Data

US 2004/0108507 A1 Jun. 10, 2004

Related U.S. Application Data

(60) Division of application No. 10/027,421, filed on Dec. 20, 2001, now Pat. No. 6,670,645, which is a continuation-in-part of application No. 09/879,014, filed on Jun. 12, 2001
(60) Provisional application No. 60/215,362, filed on Jun. 30, 2000, and provisional application No. 60/224,273, filed on Aug. 10, 2000.

(51) Int. Cl.[7] .................. H01L 33/00; H01L 35/24; H01L 51/00; H01L 21/00; H01L 51/40
(52) U.S. Cl. ................ 257/98; 257/40; 438/29; 438/69; 438/82; 438/99; 428/690; 428/917; 313/504; 546/2; 556/40; 556/136; 556/137
(58) Field of Search ................ 546/2; 556/40, 556/136, 137; 313/504; 428/690, 917; 257/40, 98; 438/29, 69, 82, 99

(56) References Cited

U.S. PATENT DOCUMENTS

| 3,718,488 | A | * | 2/1973 | Trofimenko et al. | ....... 106/1.28 |
|---|---|---|---|---|---|
| 5,552,678 | A | | 9/1996 | Tang et al. | |
| 6,303,238 | B1 | | 10/2001 | Thompson et al. | |
| 6,670,645 | B2 | | 12/2003 | Grushin et al. | |
| 6,830,828 | B2 | * | 12/2004 | Thompson et al. | ......... 428/690 |
| 2001/0019782 | A1 | | 9/2001 | Igarashi et al. | |
| 2001/0053462 | A1 | | 12/2001 | Mishima | |
| 2002/0064681 | A1 | * | 5/2002 | Takiguchi et al. | .......... 428/690 |

FOREIGN PATENT DOCUMENTS

| EP | 1175128 A2 | 1/2002 |
|---|---|---|
| EP | 1 191 614 A2 | 3/2002 |
| WO | WO 96/03410 A1 | 2/1996 |
| WO | WO 00/57676 A1 | 9/2000 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |

OTHER PUBLICATIONS

Djurovich, Peter I. et al., Ir(III) Cyclometalated Complexes As Efficient Phosphorescent Emitters In Polymer Blend and Organic LEDs, Polymer Preprints, 2000, 770–771, 41(1).

(Continued)

*Primary Examiner*—Erik Kielin

(57) ABSTRACT

The present invention is generally directed to electroluminescent Ir(III) compounds, the substituted 2-phenylpyridines, phenylpyrimidines, and phenylquinolines that are used to make the Ir(III) compounds, and devices that are made with the Ir(III) compounds.

12 Claims, 1 Drawing Sheet

OTHER PUBLICATIONS

Chatani, Naoto et al., Ru3(CO)12–Catalyzed Reaction of Pyridylbenzenes with Carbon Monoxide and Olefins. Carbonylation at a C–H Bond in the Benzene Ring, J. Org. Chem., 1997, 2604–2610, 62, American Chemical Society.

Gosmini, Corrine et al., Electrosynthesis of functionalized 2–arylpyridines from functionalized aryl and pyridine halides catalyzed by nickel bromide 2,2'–bipyridine complex, Tetrahedron Letters, 2000, 5039–5042, 41, Elsevier Science Ltd.

Cacchi, Sandro et al., The Palladium–Catalyzed Transfer Hydrogenation/Heterocyclization of B–(2–Aminophenyl–a, B–ynones. An Approach to 2–Aryl– and 2–Vinylquinolines, Synlett, 1999, 401–404, No. 4, Thieme Stuttgart, New York.

Baldo, M. A. et al., Very high–efficency green organic light–emitting devices based on electrophosphorescence, Applied Physics Letters, Jul. 5, 1999, 4–6, 75(1) American Institute of Physics.

Baldo, M. A. et al., High–efficiency fluorescent organic light–emitting devices using a phosphorescent sensitizer, Nature, Feb. 17, 2000, 750–753, 403, Macmillan Magazines Ltd.

Wang, Yue et al., (Hydroxyphenyl)pyridine derivative, its metal complexes and application as electroluminescence material, Chemical Abstracts Service, Mar. 1, 2000, Database No. 133:315395.

Dedeian, K. et al., A New Synthetic Route to the Preparation of a Series of Strong Photoreducing Agents: fac Tris–Ortho–Metalated Complexes of Iridium(III) with Substituted 2–Phenylpyridines, Inorg. Chem., 1991, 1685–1687, 30(8), American Chemical Society.

U.S. Appl. No. 60/347,910, Lecloux et al., filed Nov. 7, 2001.

U.S. Appl. No. 60.347,911, Lecloux et al., filed Nov. 7, 2001.

Lohse, Olivier, et al., The Palladium Catalysed Suzuki Coupling of 2– and 4–Chloropyridines, Synlett, 1999, 45–48, No. 1, Thieme Suttgart, New York.

Baldo, M.A. et al., Highly efficient phosphorescent emission from organic electroluminescent devices, Nature, Sep. 10, 1998, 151–154, vol. 395.

Lamansky, Sergey et al., Highly Phosphorescent Bis–Cyclometalated Iridium Complexes: Synthesis, Photophysical Characterization, and Use in Organic Light Emitting Diodes, J. Am. Chem. Soc., 2001, 4304–4312, 123, American Chemical society.

Lamansky, Sergey et al., Synthesis and Characterization of Phosphorescent Cyclometalated Iridium Complexes, Inorg. Chem. 2001, 1704–1711, 40, American Chemical Society.

Lamansky, Sergey et al., Molecularly doped polymer light emitting diodes utilizing phosphorescent Pt(II) and IR(III) dopants, Organic Electronics, 2001, 53–62, 2. Elsevier Science B.V.

Abstract of Japanese PCT Publication WO02/44189 A1, Luminescent Element and Display, Jun. 6, 2002, Canon Kabushiki Kaisha.

* cited by examiner

ELECTROLUMINESCENT IRIDIUM COMPOUNDS WITH FLUORINATED PHENYLPYRIDINES, PHENYLPYRIMIDINES, AND PHENYLQUINOLINES AND DEVICES MADE WITH SUCH COMPOUNDS

RELATED APPLICATION

Divisional of prior application No. 10/027,421 filed Dec. 20, 2001 now U.S. Pat. No. 6,670,645 which is a continuation-in-part application of U.S. patent application Ser. No. 09/879,014, filed on Jun. 12, 2001, now pending, which claims the benefit of U.S. provisional application Ser. No. 60/215,362 filed on Jun. 30, 2000 and claims the benefit of U.S. provisional application Ser. No. 60/224,273 filed on Aug. 10, 2000.

BACKGROUND OF THE INVENTION

1. Field of the Invention

This invention relates to electroluminescent complexes of iridium(III) with fluorinated phenylpyridines, phenylpyrimidines, and phenylquinolines. It also relates to electronic devices in which the active layer includes an electroluminescent Ir(III) complex.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8-hydroxyquinolate with trivalent metal ions, particularly aluminum, have been extensively used as electroluminescent components, as has been disclosed in, for example, Tang et al., U.S. Pat. No. 5,552,678.

Burrows and Thompson have reported that fac-tris(2-phenylpyridine)iridium can be used as the active component in organic light-emitting devices. (*Appl. Phys. Lett.* 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-C'$^2$, N]iridium(III). (Polymer Preprints 2000, 41(1), 770.)

However, there is a continuing need for electroluminescent compounds having improved efficiency.

SUMMARY OF THE INVENTION

The present invention is directed to an iridium compound (generally referred as "Ir(III) compounds") having at least two 2-phenylpyridine ligands in which there is at least one fluorine or fluorinated group on the ligand. The iridium compound has the following First Formula:

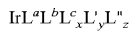
(First Formula)

where:
x=0 or 1, y=0, 1 or 2, and z=0 or 1, with the proviso that:
x=0 or y+z=0 and
when y=2 then z=0;
L'=a bidentate ligand or a monodentate ligand, and is not a phenylpyridine, phenylpyrimidine, or phenylquinoline; with the proviso that:
when L' is a monodentate ligand, y+z=2, and
when L' is a bidentate ligand, z=0;
L"=a monodentate ligand, and is not a phenylpyridine, and phenylpyrimidine, or phenylquinoline; and
$L^a$, $L^b$ and $L^c$ are alike or different from each other and each of $L^a$, $L^b$ and $L^c$ has structure (I) below:

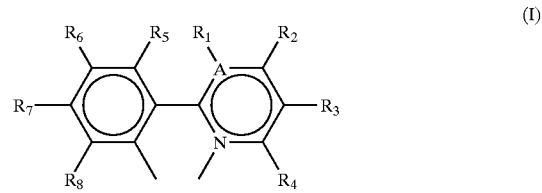
(I)

wherein:
adjacent pairs of $R_1$ through $R_4$ and $R_5$ through $R_8$ can be joined to form a five- or six-membered ring,
at least one of $R_1$ through $R_8$ is selected from F, $C_nF_{2n+1}$, $OC_nF_{2n+1}$, and $OCF_2X$, where n is an integer from 1 through 6 and X=H, Cl, or Br, and A=C or N, provided that when A=N, there is no $R_1$.

In another embodiment, the present invention is directed to substituted 2-phenylpyridine, phenylpyrimidine, and phenylquinoline precursor compounds from which the above Ir(III) compounds are made. The precursor compounds have a structure (II) or (III) below:

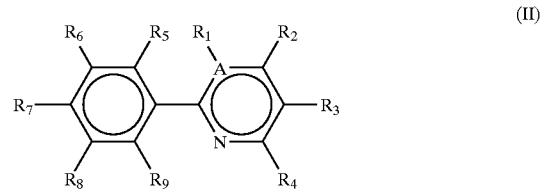
(II)

where A and $R_1$ through $R_8$ are as defined in structure (I) above,
and $R_9$ is H.

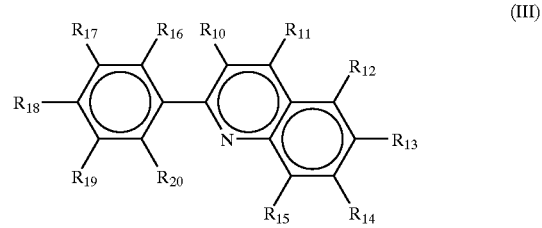
(III)

where:
at least one of $R_{10}$ through $R_{19}$ is selected from F, $C_nF_{2n+1}$, $OC_nF_{2n+1}$, and $OCF_2X$, where n=an integer between 1 and 6 and X is H, Cl, or Br, and $R_{20}$ is H.

It is understood that there is free rotation about the phenyl-pyridine, phenyl-pyrimidine and the phenyl-quinoline bonds. However, for the discussion herein, the compounds will be described in terms of one orientation.

In another embodiment, the present invention is directed to an organic electronic device having at least one emitting layer comprising the above Ir(III) compound, or combinations of the above Ir(III) compounds.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one face of the octahedron. The term "meridional" is intended to mean one isomer of a complex, $Ma_3b_3$, having octahedral geometry, in which the three "a" groups occupy three positions such that two are trans to each other. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. The term "(H+F)" is intended to mean all combinations of hydrogen and fluorine, including completely hydrogenated, partially fluorinated or perfluorinated substituents. By "emission maximum" is meant the wavelength, in nanometers, at which the maximum intensity of electroluminescence is obtained. Electroluminescence is generally measured in a diode structure, in which the material to be tested is sandwiched between two electrical contact layers and a voltage is applied. The light intensity and wavelength can be measured, for example, by a photodiode and a spectrograph, respectively.

DETAILED DESCRIPTION OF THE PREFERRED EMBODIMENTS

Figure 1:
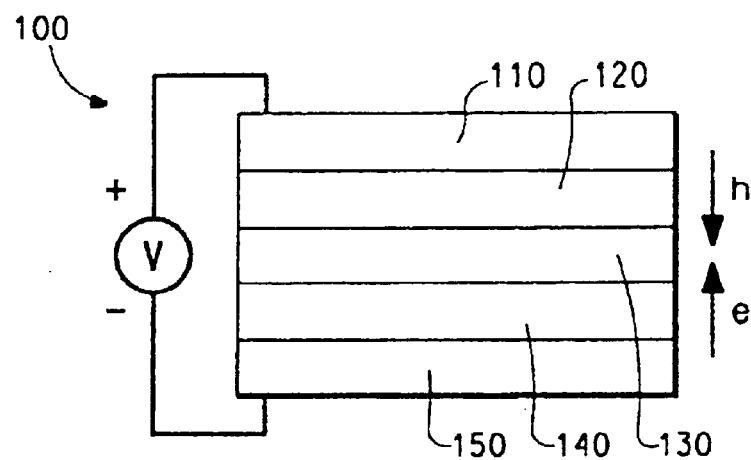
FIG. 1 is a schematic diagram of a light-emitting device (LED).

The Ir(III) compounds of the invention have the First Formula $Ir(III)L^aL^bL^c_xL'_y$ above.

The above Ir(III) compounds are frequently referred to as cyclometalated complexes: Ir(III) compounds having the following Second Formula is also frequently referred to as a bis-cyclometalated complex.:

$$IrL^aL^bL'_yL''_z \qquad \text{(Second Formula)}$$

where:

y, z, $L^a$, $L^b$, L', and L" are as defined in the First Formula above.

Ir(III) compounds having the following Third Formula is also frequently referred to as a tris-cyclometalated complex.:

$$IrL^aL^bL^c \qquad \text{(Third Formula)}$$

where:

$L^a$, $L^b$ and $L^c$ are as defined in the First Formula described above.

The preferred cyclometalated complexes are neutral and non-ionic, and can be sublimed intact. Thin films of these materials obtained via vacuum deposition exhibit good to excellent electroluminescent properties. Introduction of fluorine substituents into the ligands on the iridium atom increases both the stability and volatility of the complexes. As a result, vacuum deposition can be carried out at lower temperatures and decomposition of the complexes can be avoided. Introduction of fluorine substituents into the ligands can often reduce the non-radiative decay rate and the self-quenching phenomenon in the solid state. These reductions can lead to enhanced luminescence efficiency. Variation of substituents with electron-donating and electron-withdrawing properties allows for fine-tuning of electroluminescent properties of the compound and hence optimization of the brightness and efficiency in an electroluminescent device.

While not wishing to be bound by theory, it is believed that the emission from the iridium compounds is ligand-based, resulting from metal-to-ligand charge transfer. Therefore, compounds that can exhibit electroluminescence include those of compounds of the Second Formula $IrL^aL^bL'_yL''_z$ above, and the Third Formula $IrL^aL^bL^c$ above, where all $L^a$, $L^b$, and $L^c$ in the Third Formula are phenylpyridines, phenylpyrimidines, or phenylquinolines. The $R_1$ through $R_8$ groups of structures (I) and (II), and the $R_{10}$ through $R_{19}$ groups of structure (III) above may be chosen from conventional substitutents for organic compounds, such as alkyl, alkoxy, halogen, nitro, and cyano groups, as well as fluoro, fluorinated alkyl and fluorinated alkoxy groups. The groups can be partially or fully fluorinated (perfluorinated). Preferred iridium compounds have all $R_1$ through $R_8$ and $R_{10}$ through $R_{19}$ substituents selected from fluoro, perfluorinated alkyl ($C_nF_{2n+1}$) and perfluorinated alkoxy groups ($OC_nF_{2n+1}$), where the perfluorinated alkyl and alkoxy groups have from 1 through 6 carbon atoms, or a group of the formula $OCF_2X$, where X is H, Cl, or Br.

It has been found that the electroluminescent properties of the cyclometalated iridium complexes are poorer when any one or more of the $R_1$ through $R_8$ and $R_{10}$ through $R_{19}$ groups is a nitro group. Therefore, it is preferred that none of the $R_1$ through $R_8$ and $R_{10}$ through $R_{19}$ groups is a nitro group.

It has been found that the luminescence efficiency of the cyclometalated iridium complexes may be improved by using phenylpyridine, phenylpyrimidine, and phenylquinoline ligands in which some or all of the hydrogens have been replaced with deuterium.

The nitrogen-containing ring can be a pyridine ring, a pyrimidine or a quinoline. It is preferred that at least one fluorinated substituent is on the nitrogen-containing ring; most preferably $CF_3$.

Any conventional ligands known to transition metal coordination chemistry is suitable as the L' and L" ligands. Examples of bidentate ligands include compounds having two coordinating groups, such as ethylenediamine and acetylacetonate, which may be substituted. Examples of anionic bidentate ligands include beta-enolates, such as acetylacetonate; the anionic form of hydroxyquinolines, such as 8-hydroxyquinoline, which may be substituted, in which the H from the hydroxy group has been extracted; aminocarboxylates; iminocarboxylates, such as pyridine carboxylate; salicylates; salicylaldimines, such as 2-[(phenylimino)methyl]phenol; and phosphinoalkoxides, such as 3-(diphenylphosphino)-1-propoxide. Examples of monodentate ligands include chloride and nitrate ions; phosphines; isonitriles; carbon monoxide; and mono-amines. It is preferred that the iridium complex be neutral and sublimable. If a single bidentate ligand is used, it should have a net charge of minus one (−1). If two monodentate ligands are used, they should have a combined net charge of minus one (−1). The bis-cyclometalated complexes can be useful in preparing tris-cyclometalated complexes where the ligands are not all the same.

In a preferred embodiment, the iridium compound has the Third Formula $IrL^aL^bL^c$ as described above.

In a more preferred embodiment, $L^a=L^b=L^c$. These more preferred compounds frequently exhibit a facial geometry, as determined by single crystal X-ray diffraction, in which the nitrogen atoms coordinated to the iridium are trans with respect to carbon atoms coordinated to the iridium. These more preferred compounds have the following Fourth Formula:

fac-Ir(L$^a$)$_3$  (Fourth Formula)

where $L^a$ has structure (I) above.

The compounds can also exhibit a meridional geometry in which two of the nitrogen atoms coordinated to the iridium are trans to each other. These compounds have the following Fifth Formula:

mer-Ir(L$^a$)$_3$  (Fifth Formula)

where $L^a$ has structure (I) above.

Examples of compounds of the Fourth Formula and Fifth Formula above are given in Table 1 below:

Examples compounds of the Second Formula $IrL^aL^bL'_yL''_z$ above include compounds 1-n, 1-o, 1-p 1-w and 1-x, respectively having structure (IV), (V), (VI), (IX) and (X) below:

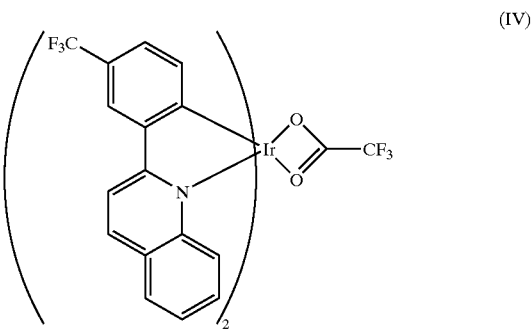

(IV)

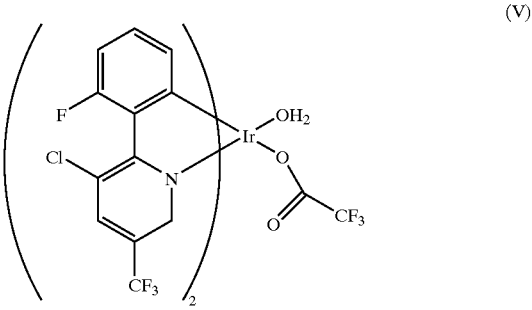

(V)

TABLE 1

| Compound | A | $R_1$ | $R_2$ | $R_3$ | $R_4$ | $R_5$ | $R_6$ | $R_7$ | $R_8$ | Formula |
|---|---|---|---|---|---|---|---|---|---|---|
| 1-a | C | H | H | CF$_3$ | H | H | H | H | H | Fourth |
| 1-b | C | H | H | CF$_3$ | H | H | H | F | H | Fourth |
| 1-c | C | H | H | CF$_3$ | H | F | H | H | H | Fourth |
| 1-d | C | H | H | H | H | F | H | H | H | Fourth |
| 1-e | C | H | H | CF$_3$ | H | H | CF$_3$ | H | H | Fourth |
| 1-f | C | H | H | H | H | H | CF$_3$ | H | H | Fourth |
| 1-g | C | H | H | H | H | H | H | F | H | Fourth |
| 1-h | C | Cl | H | CF$_3$ | H | H | H | H | H | Fourth |
| 1-i | C | H | H | CF$_3$ | H | H | H | OCH$_3$ | H | Fourth |
| 1-j | C | H | H | CF$_3$ | H | H | F | H | H | Fourth |
| 1-k | C | H | H | NO$_2$ | H | H | CF$_3$ | H | H | Fourth |
| 1-l | C | H | H | CF$_3$ | H | H | H | OCF$_3$ | H | Fourth |
| 1-m | N | — | CF$_3$ | H | H | H | H | F | H | Fourth |
| 1-q | C | H | H | CF$_3$ | H | H | OCH$_3$ | H | H | Fourth |
| 1-r | C | H | OCH$_3$ | H | H | H | H | CF$_3$ | H | Fourth |
| 1-s | C | H | H | H | H | F | H | F | H | Fourth and Fifth |
| 1-t | C | H | H | CF$_3$ | H | H | F | H | F | Fifth |
| 1-u | C | H | H | CF$_3$ | H | F | H | F | H | Fifth |
| 1-v | C | H | H | CF$_3$ | H | H | H | F | H | Fifth |

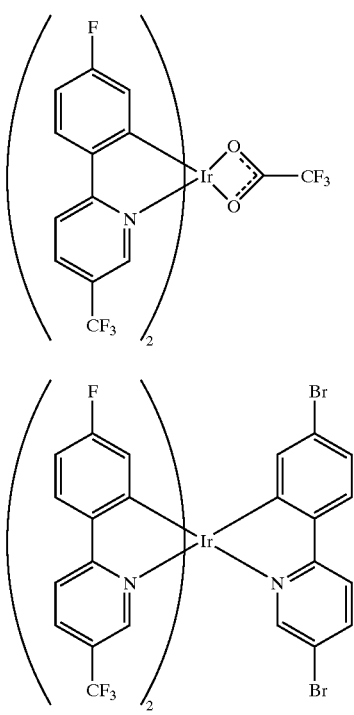

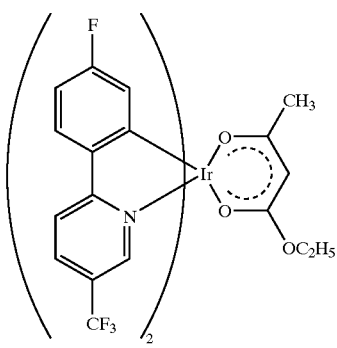

The iridium complexes of the Third Formula $IrL^aL^bL^c$ above are generally prepared from the appropriate substituted 2-phenylpyridine, phenylpyrimidine, or phenylquinoline. The substituted 2-phenylpyridines, phenylpyrimidines, and phenylquinolines, as shown in Structure (II) above, are prepared, in good to excellent yield, using the Suzuki coupling of the substituted 2-chloropyridine, 2-chloropyrimidine or 2-chloroquinoline with arylboronic acid as described in O. Lohse, P. Thevenin, E. Waldvogel *Synlett*, 1999, 45–48. This reaction is illustrated for the pyridine derivative, where X and Y represent substituents, in Equation (1) below:

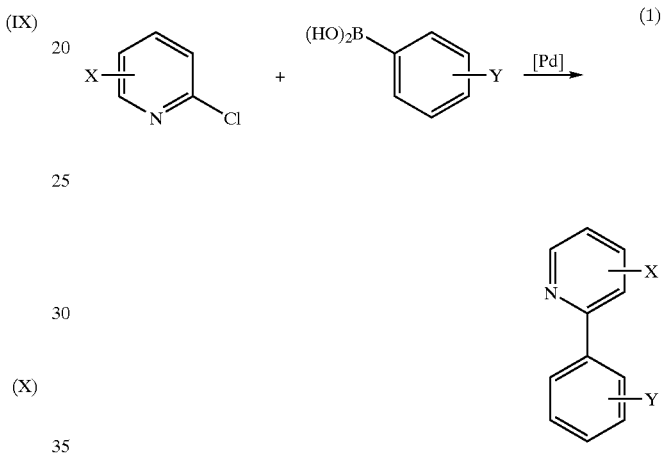

Examples of 2-phenylpyridine and 2-phenylpyrimidine compounds, having structure (II) above, are given in Table 2 below:

TABLE 2

| Compound | A | $R_1$ | $R_2$ | $R_3$ | $R_4$ | $R_5$ | $R_6$ | $R_7$ | $R_8$ | $R_9$ |
|---|---|---|---|---|---|---|---|---|---|---|
| 2-a | C | H | H | $CF_3$ | H | F | H | H | H | H |
| 2-b | C | H | H | $CF_3$ | H | H | $CF_3$ | H | H | H |
| 2-c | C | H | H | $NO_2$ | H | H | $CF_3$ | H | H | H |
| 2-d | C | H | H | $CF_3$ | H | H | F | H | H | H |
| 2-e | C | H | H | $CF_3$ | H | H | H | $CH_3O$ | H | H |
| 2-f | C | Cl | H | $CF_3$ | H | H | H | H | H | H |
| 2-g | C | H | H | H | $CH_3$ | H | H | F | H | H |
| 2-h | N | — | H | H | H | H | H | F | H | H |
| 2-i | C | H | H | $CF_3$ | H | H | H | $CF_3O$ | H | H |
| 2-j | N | — | $CF_3$ | H | H | F | H | H | H | H |
| 2-k | C | H | H | $CF_3$ | H | H | H | F | H | H |
| 2-l | C | $CF_3$ | H | H | H | H | H | H | H | H |
| 2-m | C | Cl | H | $CF_3$ | H | H | H | F | H | H |
| 2-n | C | $CF_3$ | H | H | H | H | H | F | H | H |
| 2-o | C | $CF_3$ | H | H | H | H | H | $CH_3O$ | H | H |
| 2-p | C | Cl | H | $CF_3$ | H | H | H | $CH_3O$ | H | H |
| 2-q | N | — | $CF_3$ | H | H | H | H | F | H | H |

TABLE 2-continued

| Compound | A | $R_1$ | $R_2$ | $R_3$ | $R_4$ | $R_5$ | $R_6$ | $R_7$ | $R_8$ | $R_9$ |
|---|---|---|---|---|---|---|---|---|---|---|
| 2-r | C | Cl | H | $CF_3$ | H | H | H | H | H | F |
| 2-s | C | H | H | $CF_3$ | H | H | H | H | H | H |
| 2-t | C | Cl | H | H | H | F | H | H | H | H |
| 2-v | C | H | H | $CF_3$ | H | H | $CH_3O$ | H | H | H |
| 2-w | C | H | $CH_3O$ | H | H | H | H | $CF_3$ | H | H |
| 2-x | C | H | H | H | H | H | F | F | H | H |
| 2-y | C | H | H | $CF_3$ | H | H | F | H | F | H |
| 2-z | C | H | H | $CF_3$ | H | F | H | F | H | H |
| 2-aa | C | H | H | Br | H | H | H | Br | H | H |

One example of a substituted 2-phenylquinoline compound, having structure (III) above, is compound 2-u, which has $R_{17}$ is $CF_3$ and $R_{10}$ through $R_{16}$ and $R_{18}$ through $R_{20}$ are H.

The 2-phenylpyridines, pyrimidines, and quinolines thus prepared are used for the synthesis of the cyclometalated iridium complexes. A convenient one-step method has been developed employing commercially available iridium trichloride hydrate and silver trifluoroacetate. The reactions are generally carried out with an excess of 2-phenylpyridine, pyrimidine, or quinoline, without a solvent, in the presence of 3 equivalents of $AgOCOCF_3$. This reaction is illustrated for a 2-phenylpyridine in Equation (2) below:

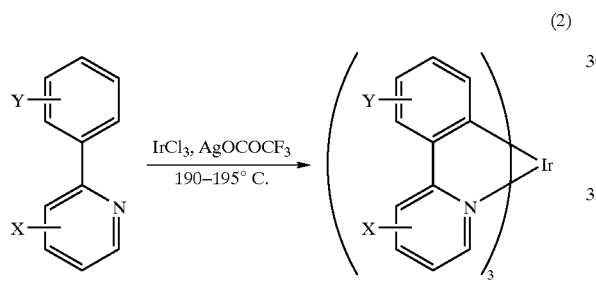

(2)

The tris-cyclometalated iridium complexes were isolated, purified, and fully characterized by elemental analysis, $^1H$ and $^{19}F$ NMR spectral data, and, for compounds 1-b, 1-c, and 1-e, single crystal X-ray diffraction. In some cases, mixtures of isomers are obtained. Often the mixture can be used without isolating the individual isomers.

The iridium complexes having the Second Formula $IrL^a\text{-}L^bL'_yL''_z$ above, may, in some cases, be isolated from the reaction mixture using the same synthetic procedures as preparing those having Third Formula $IrL^aL^bL^c$ above. The complexes can also be prepared by first preparing an intermediate iridium dimer having structure (VII) below:

(VII)

wherein:
B=H, $CH_3$, or $C_2H_5$, and
$L^a$, $L^b$, $L^c$, and $L^d$ can be the same or different from each other and each of $L^a$, $L^b$, $L^c$, and $L^d$ has structure (I) above.

The iridium dimers can generally be prepared by first reacting iridium trichloride hydrate with the 2-phenylpyridine, phenylpyrimidine or phenyiquinoline, and adding NaOB.

One particularly useful iridium dimer is the hydroxo iridium dimer, having structure (VIII) below:

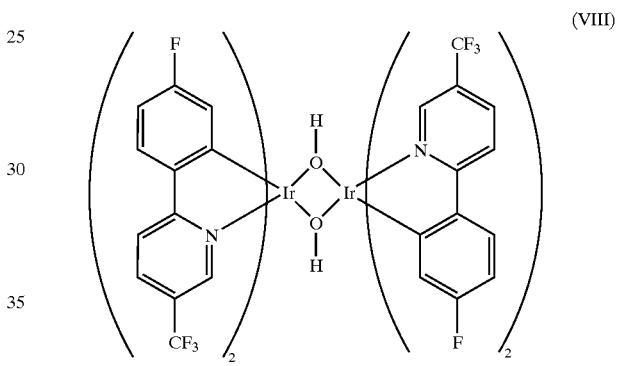

(VIII)

This intermediate can be used to prepare compound 1-p by the addition of ethyl acetoacetate.

Of particular interest, are complexes in which the emission has a maximum in the red region of the visible spectrum, from 570 to 625 nm for red-orange, and from 625 to 700 nm for red. It has been found that the emission maxima of complexes of the Second and Third Formulae are shifted to the red when L has structure (XI) below, derived from a phenyl-quinoline compound having structure (III) above, or when L has structure (XII) below, derived from a phenyl-isoquinoline compound:

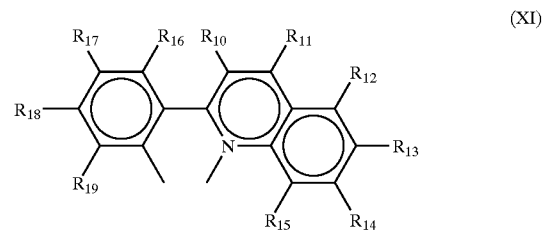

(XI)

where:
at least one of $R_{10}$ through $R_{19}$ is selected from F, $C_nF_{2n+1}$, $OC_nF_{2n+1}$, and $OCF_2X$, where n is an integer from 1 through 6 and X is H, Cl, or Br;

(XII)

where:
at least one of $R_{21}$ through $R_{30}$ is selected from F, $C_nF_{2n+1}$, $OC_nF_{2n+1}$, and $OCF_2X$, where n is an integer from 1 through 6 and X is H, Cl, or Br.

It has also been found that the ligands of the invention can have perfluoroalkyl and perfluoroalkoxy substituents with up to 12 carbon atoms.

In the Second Formula, the L' and L" ligands in the complex can be selected from any of those listed above, and are preferably chosen so that the overall molecule is uncharged. Preferably, z is 0, and L' is a monoanionic bidentate ligand, that is not a phenylpyridine, phenyhlpyrimidine, or phenylquinoline.

Although not preferred, complexes of the Second Formula also have emission maxima that are shifted to the red when L is a phenylpyridine ligand with structure (I) above, and L' is a bidentate hydroxyquinolate ligand.

Examples of compounds of the Second Formula, where $L^a$ is the same as $L^b$, L' is a bidentate ligand, y is 1, and z is 0, and compounds of the Third Formula where $L^a$, $L^b$, and $L^c$ are the same, are given in Table 8 below. When L has structure (I) above, A is C. In this table, "acac" stands for 2,4-pentanedionate; "8hq" stands for 8-hydroxyquinolinate; "Me-8hq" stands for 2-methyl-8-hydroxyquinolinate.

TABLE 8

| Compound | Complex Formula | Ligand Structure | R substituents | L' |
|---|---|---|---|---|
| 8-a | Second | I | $R_3$ = $CF_3$<br>$R_7$ = F | Me-8hq |
| 8-b | Second | I | $R_3$ = $CF_3$<br>$R_7$ = F | 8hq |
| 8-c | Second | XI | $R_{18}$ = $CF_3$ | acac |
| 8-d | Second | XII | $R_{29}$ = $CF_3$ | acac |
| 8-e | Second | XII | $R_{28}$ = $CF_3$ | acac |
| 8-f | Second | XII | $R_{29}$ = F | acac |
| 8-g | Second | XII | $R_{27}$ = F<br>$R_{29}$ = F | acac |
| 8-h | Second | XII | $R_{27}$ = F<br>$R_{29}$ = F<br>$R_{30}$ = F | acac |
| 8-i | Second | XII | $R_{28}$ = F<br>$R_{29}$ = F<br>$R_{30}$ = F | acac |
| 8-j | Second | XII | $R_{28}$ = F<br>$R_{30}$ = F | acac |
| 8-k | Second | XII | $R_{29}$ = $C_8F_{17}$ | acac |
| 8-l | Third | XII | $R_{29}$ = $CF_3$ | — |
| 8-m | Third | XII | $R_{28}$ = F<br>$R_{29}$ = F<br>$R_{30}$ = F | — |
| 8-n | Third | XII | $R_{27}$ = F<br>$R_{29}$ = F<br>$R_{30}$ = F | — |
| 8-o | Third | XII | $R_{27}$ = F<br>$R_{29}$ = F | — |
| 8-p | Third | XII | $R_{28}$ = $CF_3$ | — |
| 8-q | Third | XII | $R_{28}$ = F<br>$R_{30}$ = F | — |
| 8-r | Second | XII | $R_{27}$ = F<br>$R_{29}$ = F | acac |
| 8-s | Second | XII | $R_{29}$ = $OCF_3$ | acac |

The complexes in Table 8 have emission maxima in the range of about 590 to 650 nm.

Also of particular interest, are complexes in which the emission has a maximum in the blue region of the visible spectrum, from about 450 to 500 nm. It has been found that the photoluminescence and electroluminescence of the complexes are shifted to the blue when the complex has the Second Formula where $L^a$ and $L^b$ are phenyl-pyridine ligands with an additional ligand selected from a phosphine, an isonitrile, and carbon monoxide. Suitable complexes have the Sixth Formula below:

$$IrL^aL^bL'L''$$ (Sixth Formula)

where

L' is selected from a phosphine, an isonitrile, and carbon monoxide;

L" is selected from F, Cl, Br, and I $L^a$ and $L^b$ are alike or different and each of $L^a$ and $L^b$ has structure (I) above, wherein:
$R_1$ through $R_8$ are independently selected from alkyl, alkoxy, halogen, nitro, cyano, fluoro, fluorinated alkyl and fluorinated alkoxy groups, and at least one of $R_1$ through $R_8$ is selected from F, $C_nF_{2n+1}$, $OC_nF_{2n+1}$, and $OCF_2X$, where n is an integer from 1 through 6 and X is H, Cl, or Br, and
A is C.

The phosphine ligands in the Sixth Formula preferably have the Seventh Formula below $$P(Ar)_3$$ (Seventh Formula)

where Ar is an aromatic group, preferably a phenyl group, which may have alkyl or aryl substituents. Most preferably, the Ar group is a phenyl group having at least one fluorine or fluorinated alkyl substituent. Examples of suitable phosphine ligands include (with the abbreviation provided in brackets):

triphenylphosphine [PPh3]
tris[3,5-bis(trifluoromethyl)phenyl]phosphine[PtmPh3]

Some of the phosphine compounds are available commercially, or they can be prepared using any of numerous well-known synthetic procedures, such as alkylation or arylation reactions of $PCl_3$ or other P-electrophiles with organolithium or organomagnesium compounds.

The isonitrile ligands in the Sixth Formula, preferably have isonitrile substituents on aromatic groups. Examples of suitable isonitrile ligands include (with the abbreviation provided in brackets):

2,6-dimethylphenyl isocyanide [NC-1]
3-trifluoromethylphenyl isocyanide [NC-2]
4-toluenesulfonylmethyl isocyanide [NC-3]

Some of the isonitrile compounds are available commercially. They also can be prepared using known procedures, such as the Hofmann reaction, in which the dichlorocarbene is generated from chloroform and a base in the presence of a primary amine.

It is preferred that L" in the Sixth Formula is chloride. It is preferred that $L^a$ is the same as $L^b$.

Examples of compounds of the Sixth Formula where $L^a$ is the same as $L^b$ and L" is chloride, are given in Table 9 below, where $R_1$ through $R_8$ are as shown in structure (I) above.

TABLE 9

| Comp. | L' | $R_1$ | $R_2$ | $R_3$ | $R_4$ | $R_5$ | $R_6$ | $R_7$ | $R_8$ |
|---|---|---|---|---|---|---|---|---|---|
| 9-a | NC-1 | H | $CH_3$ | H | H | F | H | F | H |
| 9-b | NC-1 | H | H | $CH_3$ | H | F | H | F | H |
| 9-c | NC-1 | H | H | H | H | F | H | F | H |
| 9-d | NC-1 | H | H | H | H | H | $CF_3$ | H | H |
| 9-e | NC-1 | H | $CH_3$ | H | H | H | $CF_3$ | H | H |
| 9-f | NC-1 | H | H | $CF_3$ | H | H | H | F | H |
| 9-g | NC-1 | H | H | $CF_3$ | H | H | $CF_3$ | H | H |
| 9-h | NC-2 | H | H | H | H | H | $CF_3$ | H | H |
| 9-i | NC-3 | H | H | $CF_3$ | H | H | H | F | H |
| 9-j | PPh3 | H | H | $CF_3$ | H | H | H | F | H |
| 9-k | PtmPh3 | H | H | $CF_3$ | H | H | H | F | H |
| 9-l | CO | H | H | $CF_3$ | H | H | H | F | H |

NC-1 is 2,6-$(CH_3)_2C_6H_3NC$;
NC-2 is 3-$CF_3C_6H_4NC$;
NC-3 is 4-$CH_3C_6H_4SO_2CH_2NC$;
$PPh_3$ is $P(C_6H_5)_3$
$PtmPh_3$ is $(Ar_f)_3P$, where $Ar_f$ = 3,5-$(CF_3)_2C_6H_3$;

The complexes in Table 9 have emission maxima in the range of about 450 to 550 nm.

Electronic Device

The present invention also relates to an electronic device comprising at least one photoactive layer positioned between two electrical contact layers, wherein the at least one layer of the device includes the iridium complex of the invention. Devices frequently have additional hole transport and electron transport layers. A typical structure is shown in FIG. 1. The device 100 has an anode layer 110 and a cathode layer 150. Adjacent to the anode is a layer 120 comprising hole transport material. Adjacent to the cathode is a layer 140 comprising an electron transport material. Between the hole transport layer and the electron transport layer is the photoactive layer 130. Layers 120, 130, and 140 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The iridium compounds of the invention are particularly useful as the photoactive material in layer 130, or as electron transport material in layer 140. Preferably the iridium complexes of the invention are used as the light-emitting material in diodes. It has been found that in these applications, the fluorinated compounds of the invention do not need to be in a solid matrix diluent in order to be effective. A layer that is greater than 20% by weight iridium compound, based on the total weight of the layer, up to 100% iridium compound, can be used as the emitting layer. This is in contrast to the non-fluorinated iridium compound, tris(2-phenylpyridine) iridium (III), which was found to achieve maximum efficiency when present in an amount of only 6 to 8% by weight in the emitting layer. This was necessary to reduce the self-quenching effect. Additional materials can be present in the emitting layer with the iridium compound. For example, a fluorescent dye may be present to alter the color of emission. A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the iridium compound is generally present in a small amount, usually less than 20% by weight, preferably less than 10% by weight, based on the total weight of the layer.

In some cases the iridium complexes may be present in more than one isomeric form, or mixtures of different complexes may be present. It will be understood that in the above discussion of OLEDs, the term "the iridium compound" is intended to encompass mixtures of compounds and/or isomers.

To achieve a high efficiency LED, the HOMO (highest occupied molecular orbital) of the hole transport material should align with the work function of the anode, the LUMO (lowest unoccupied molecular orbital) of the electron transport material should align with the work function of the cathode. Chemical compatibility and sublimation temp of the materials are also important considerations in selecting the electron and hole transport materials.

The other layers in the OLED can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Group 8 through 10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1 through 18 (CRC Handbook of Chemistry and Physics, 81$^{st}$ Edition, 2000). The anode 110 may also comprise an organic material such as polyaniline as described in "Flexible light-emitting diodes made from soluble conducting polymer," *Nature* vol. 357, pp 477–479 (11 Jun. 1992). At least one of the anode and cathode should be at least partially transparent to allow the generated light to be observed.

Examples of hole transport materials for layer 120 have been summarized for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine(TPD), 1,1-bis [(di-4-tolylamino)phenyl]cyclohexane(TAPC), N,N'-bis(4-methylphenyl)-N,N'-bis(4-ethylphenyl)-[1,1'-(3,3'-dimethyl)biphenyl]-4,4'-diamine(ETPD), tetrakis-(3-methylphenyl)-N,N,N',N'-2,5-phenylenediamine(PDA), a-phenyl-4-N,N-diphenylaminostyrene(TPS), p-(diethylamino)benzaldehyde diphenylhydrazone(DEH), triphenylamine(TPA), bis[4-(N,N-diethylamino)-2-methylphenyl](4-methylphenyl)methane (MPMP), 1-phenyl-3-[p-(diethylamino)styryl]-5-[p-(diethylamino) phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, and polyaniline. It is also possible to obtain hole transporting polymers by doping hole transporting molecules such as those mentioned above into polymers such as polystyrene and polycarbonate.

Examples of electron transport materials for layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500 to 5000 Å, preferably 1000 to 2000 Å; hole transport layer 120, 50 to 1000 Å, preferably 200 to 800 Å; light-emitting layer 130, 10 to 1000 Å, preferably 100 to 800 Å; electron transport layer 140, 50 to 1000 Å, preferably 200 to 800 Å; cathode 150, 200 to 10000 Å, preferably 300 to 5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the iridium compounds of the invention, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The iridium complexes of the invention often are phosphorescent and photoluminescent and may be useful in applications other than OLEDs. For example, organometallic complexes of iridium have been used as oxygen sensitive indicators, as phosphorescent indicators in bioassays, and as catalysts. The bis cyclometalated complexes can be used to sythesize tris cyclometalated complexes where the third ligand is the same or different.

EXAMPLES

The following examples illustrate certain features and advantages of the present invention. They are intended to be illustrative of the invention, but not limiting. All percentages are by weight, unless otherwise indicated.

Example 1

This example illustrates the preparation of the 2-phenylpyridines and 2-phenylpyrimidines which are used to form the iridium compounds.

The general procedure used was described in O. Lohse, P. Thevenin, E. Waldvogel *Synlett*, 1999, 45–48. In a typical experiment, a mixture of 200 mL of degassed water, 20 g of potassium carbonate, 150 mL of 1,2-dimethoxyethane, 0.5 g of $Pd(PPh_3)_4$, 0.05 mol of a substituted 2-chloropyridine (quinoline or pyrimidine) and 0.05 mol of a substituted phenylboronic acid was refluxed (80–90° C.) for 16 to 30 h. The resulting reaction mixture was diluted with 300 mL of water and extracted with $CH_2Cl_2$ (2×100 mL). The combined organic layers were dried over $MgSO_4$, and the solvent removed by vacuum. The liquid products were purified by fractional vacuum distillation. The solid materials were recrystallized from hexane. The typical purity of isolated materials was >98%. The starting materials, yields, melting and boiling points of the new materials are given in Table 3. NMR data and analytical data are given in Table 4.

TABLE 3

Preparation of 2-Phenyl Pyridines, Phenylpyrimidines and Phenylquinolines

| Compound | Yield in % | B.p./mm Hg (m.p.) in ° C. |
|---|---|---|
| 2-s | 70 | — |
| 2-a | 72 | — |
| 2-b | 48 | — |
| 2-u | 75 | (76–78) |
| 2-c | 41 | (95–96) |
| 2-d | 38 | (39–40) |
| 2-e | 55 | 74.5/0.1 |
| 2-g | 86 | 71–73/0.07 |
| 2-t | 65 | 77–78/0.046 |
| 2-k | 50 | (38–40) |
| 2-m | 80 | 72–73/0.01 |
| 2-f | 22 | 52–33/0.12 |

TABLE 3-continued

Preparation of 2-Phenyl Pyridines, Phenylpyrimidines and Phenylquinolines

| Compound | Yield in % | B.p./mm Hg (m.p.) in ° C. |
|---|---|---|
| 2-v | 63 | 95–96/13 |
| 2-w | 72 | |
| 2-x | 35 | 61–62/0.095 |
| 2-y | 62 | (68–70) |
| 2-z | 42 | 66–67/0.06 (58–60) |
| 2-aa | 60 | |

TABLE 4

Properties of 2-Phenyl Pyridines, Phenylpyrimidines and Phenylquinolines

| Compound | $^1$H NMR | $^{19}$F NMR | Analysis %, found (calc.) or MS (M$^+$) |
|---|---|---|---|
| 2-s | 7.48(3H), 7.70(1H), 7.83(1H), 7.90(2H), 8.75(1H) | −62.68 | C, 64.50 (64.57) H, 3.49 (3.59) N, 6.07(6.28) |
| 2-a | 7.19(1H), 7.30(1H), 7.43(1H), 7.98(2H), 8.07(1H) 9.00(1H) | −60.82(3F, s), −116.96(1F, m) | C, 59.56 (59.75) H, 3.19 (2.90) N, 5.52 (5.81) |
| 2-b | 7.58(1H), 7.66(1H), 7.88(1H), 8.03(1H), 8.23(1H), 8.35(1H) 8.99(1H) | −62.75(3F, s), −63.10(3F, s) | C, 53.68 (53.60) H, 2.61 (2.40) N, 4.53 (4.81) |
| 2-u | 7.55(1H), 7.63(1H), 7.75(2H), 7.89(2H), 8.28(2H), 8.38(1H) 8.50(1H) | −62.89(s) | C, 69.17 (70.33) H, 3.79 (3.66) N, 4.88 (5.12) |
| 2-c | 7.53(1H), 7.64(1H), 7.90(1H), 8.18(1H), 8.30(1H), 8.53(1H), 9.43(1H) | −62.14(s) | C, 53.83(53.73) H, 2.89 (2.61) N, 9.99 (10.44) |
| 2-d | 7.06(1H), 7.48(1H), 7.81(3H), 8.01(1H), 8.95(1H), | −62.78(3F, s), −112.61 (1F, m) | C, 59.73 (59.75) H, 2.86 (2.90) N, 5.70 (5.81) |
| 2-e | 3.80(3H) 6.93(2H), 7.68(1H), 7.85(1H), 7.96(2H), 8.82(1H) | −62.63 (s) | C, 61.66 (61.90) H, 3.95 (4.04) N, 5.53 (5.38) |
| 2-g | 2.70(3H) 7.10(3H), 7.48(1H), 7.60(1H), 8.05(2H), | −114.03 (m) | C, 76.56 (77.00) H, 5.12 (5.30) N, 5.43 (7.50) |
| 2-t | 7.10(2H), 7.35(2H), 7.96(1H), 8.78(1H) | −62.73 (3F, s), −113.67 (1F, m) | C, 50.51 (52.17) H, 1.97 (2.17) N, 5.09 (5.07) |
| 2-k | 7.08(2H), 7.62(1H), 7.90(3H), 8.80(1H), | −62.75 (3F, s), −111.49 (m) | C, 60.39 (59.75), H, 3.38 (2.90), N, 5.53 (5.51) |
| 2-m | 7.10(2H), 7.80(2H), 8.00(1H), 8.75(1H), | −62.63 (3F, s), −111.24 (m) | C, 52.13 (52.17) H, 2.16 (2.17) N, 4.85 (5.07) |
| 2-f | 7.55(3H), 7.77(2H), 8.06(1H), 8.87(1H) | −62.57(s) | 257(M$^+$, C$_{12}$H$_7$F$_3$ClN$^+$), 222(M-Cl) |
| 2-v | 3.8(3H), 6.95(1H), 7.30(1H), 7.50(1H), 7.58(1H), 7.75(1H), 7.90(1H), 8.87(1H) | −62.70 ppm | C, 61.66(61.37), H, 3.98(3.67), N, 5.53(5.48) |
| 2-w | 8.54(1H, d), 8.21(2H, d), 7.70(2H, d), 7.24(1H, s), 6.82(1H, dd), 3.91 (3H, s) | −63.08(3F, s) | |
| 2-x | 6.9(2H, m), 7.18(2H, m), 7.68(2H, m), 7.95(1H, m), 8.65(1H, m); | −109.70(1F, m), −113.35(1F, m). | |
| 2-y | 6.94(1H), 7.62(2H), 7.82(1H), 8.03(1H), 8.96(1H); | −62.72(3F, s), −109.11(2F, m) | |
| 2-z | 6.85(1H), 6.93(1H), 7.80, 7.90, 8.05(3H), 8.89(1H); | −62.80(3F, s), −107.65(1F, m), −112.45(1F, m). | |
| 2-aa | 7.70(3H, m), 7.85(3H, m), 7.80, 7.90, 8.85(1H, m). | | |

Example 2

This example illustrates the preparation of iridium compounds of the Fourth Formula fac-Ir(L$^a$)$_3$ above.

In a typical experiment, a mixture of IrCl$_3$.nH$_2$O (53–55% Ir), AgOCOCF$_3$ (3.1 equivalents per Ir), 2-arylpyridine (excess), and (optionally) a small amount of water was vigorously stirred under N$_2$ at 180–195° C. (oil bath) for 2 to 8 hours. The resulting mixture was thoroughly extracted with CH$_2$Cl$_2$ until the extracts were colorless. The extracts were filtered through a silica column to produce a clear yellow solution. Evaporation of this solution gave a residue which was treated with methanol to produce colored crystalline tris-cyclometalated Ir complexes. The complexes were separated by filtration, washed with methanol, dried under vacuum, and (optionally) purified by crystallization, vacuum sublimation, or Soxhlet extraction. Yields: 10–82%.

All materials were characterized by NMR spectroscopic data and elemental analysis, and the results are given in Table 5 below. Single-crystal X-ray structures were obtained for three complexes of the series.

Compound 1-b

A mixture of $IrCl_3 \cdot nH_2O$ (54% Ir; 508 mg), 2-(4-fluorophenyl)-5-trifluoromethylpyridine, compound kk (2.20 g), $AgOCOCF_3$ (1.01 g), and water (1 mL) was vigorously stirred under a flow of $N_2$ as the temperature was slowly (30 min) brought up to 185° C. (oil bath). After 2 hours at 185–190° C. the mixture solidified. The mixture was cooled down to room temperature. The solids were extracted with dichloromethane until the extracts decolorized. The combined dichloromethane solutions were filtered through a short silica column and evaporated. After methanol (50 mL) was added to the residue the flask was kept at –10° C. overnight. The yellow precipitate of the tris-cyclometalated complex, compound b, was separated, washed with methanol, and dried under vacuum. Yield: 1.07 g (82%). X-Ray quality crystals of the complex were obtained by slowly cooling its warm solution in 1,2-dichloroethane.

Compound 1-e

A mixture of $IrCl_3 \cdot nH_2O$ (54% Ir; 504 mg), 2-(3-trifluoromethylphenyl)-5-trifluoromethylpyridine, compound bb (1.60 g), and $AgOCOCF_3$ (1.01 g) was vigorously stirred under a flow of $N_2$ as the temperature was slowly (15 min) brought up to 192° C. (oil bath). After 6 hours at 190–195° C. the mixture solidified. The mixture was cooled down to room temperature. The solids were placed on a silica column which was then washed with a large quantity of dichloromethane. The residue after evaporation of the filtrate was treated with methanol to produce yellow solid. The solid was collected and purified by extraction with dichloromethane in a 25-mL micro-Soxhlet extractor. The yellow precipitate of the tris-cyclometalated complex, compound e, was separated, washed with methanol, and dried under vacuum. Yield: 0.59 g (39%). X-Ray quality crystals of the complex were obtained from hot 1,2-dichloroethane.

Compound 1-d

A mixture of $IrCl_3 \cdot nH_2O$ (54% Ir; 508 mg), 2-(2-fluorophenyl)-5-trifluoromethylpyridine, compound aa (1.53 g), and $AgOCOCF_3$ (1.01 g) was vigorously stirred under a flow of $N_2$ at 190–195° C. (oil bath) for 6 h 15 min. The mixture was cooled down to room temperature and then extracted with hot 1,2-dichloroethane. The extracts were filtered through a short silica column and evaporated. Treatment of the residue with methanol (20 mL) resulted in precipitation of the desired product, compound d, which was separated by filtration, washed with methanol, and dried under vacuum. Yield: 0.63 g (49%). X-Ray quality crystals of the complex were obtained from dichloromethane/methanol.

Compound 1-i

A mixture of $IrCl_3 \cdot nH_2O$ (54% Ir; 503 mg), 2-(4-trifluoromethoxyphenyl)-5-trifluoromethylpyridine, compound ee (2.00 g), and $AgOCOCF_3$ (1.10 g) was vigorously stirred under a flow of $N_2$ at 190–195° C. (oil bath) for 2 h 45 min. The mixture was cooled down to room temperature and then extracted with dichloromethane. The extracts were filtered through a short silica column and evaporated. Treatment of the residue with methanol (20 mL) resulted in precipitation of the desired product, compound i, which was separated by filtration, washed with methanol, and dried under vacuum. The yield was 0.86 g. Additionally, 0.27 g of the complex was obtained by evaporating the mother liquor and adding petroleum ether to the residue. Overall yield: 1.13 g (72%).

Compound 1-q

A mixture of $IrCl_3 \cdot nH_2O$ (54% Ir; 530 mg), 2-(3-methoxyphenyl)-5-trifluoromethylpyridine (2.50 g), $AgOCOCF_3$ (1.12 g), and water (1 mL) was vigorously stirred under a flow of $N_2$ as the temperature was slowly (30 min) brought up to 185° C. (oil bath). After 1 hour at 185° C. the mixture solidified. The mixture was cooled down to room temperature. The solids were extracted with dichloromethane until the extracts decolorized. The combined dichloromethane solutions were filtered through a short silica column and evaporated. The residue was washed with hexanes and then recrystallized from 1,2-dichloroethane—hexanes (twice). Yield: 0.30 g. $^{19}F$ NMR ($CD_2Cl_2$, 20° C.), δ: –63 (s). $^1H$ NMR ($CD_2Cl_2$, 20° C.), δ: 8.1(1H), 7.9 (1H), 7.8 (1H), 7.4 (1H), 6.6 (2H), 4.8 (3H). X-Ray quality crystals of the complex (1,2-dichloroethane, hexane solvate) were obtained from 1,2-dichloroethane—hexanes. This facial complex was orange-photoluminescent.

Compounds 1-a, 1-c, 1-f through 1-h, 1-j through 1-m, and 1-r were similarly prepared. In the preparation of compound 1-i, a mixture of isomers was obtained with the fluorine in either the $R_6$ or $R_8$ position.

TABLE 5

| Compound | Analysis (calcd (found)) | NMR ($CD_2Cl_2$, 25° C.) |
|---|---|---|
| 1-a | C: 50.3(50.1) H: 2.5(2.7) N: 4.9(4.9) Cl: 0.0(0.2) | $^1H$: 6.8(1H), 6.9(1H), 7.0(1H), 7.8(2H), 7.95(1H), 8.1(1H) $^{19}F$: –63.4 |
| 1-b | C: 47.4(47.3) H: 2.0(2.1) N: 4.6(4.4) | $^1H$: 6.4(1H), 6.75(1H), 7.7(1H), 7.8 (1H), 7.95(1H), 8.05(1H) $^{19}F$: –63.4(s); –109.5(ddd) |
| 1-c | C: 47.4(47.2) H: 2.0(2.0) N: 4.6(4.5) | $^1H$: 6.6(1H), 6.7(1H), 6.9(1H), 7.8 (1H), 8.0(1H), 8.6(1H) $^{19}F$: –63.5(s); –112.8(ddd) |
| 1-d | C: 55.9(56.1) H: 3.0(3.2) N: 5.9(5.8) | $^1H$: 6.6(2H), 6.8(1H), 7.0(1H), 7.6 (1H), 7.7(1H), 8.4(1H) $^{19}F$: –115.0(ddd) |
| 1-e | C: 44.1(43.3) H: 1.7(2.1) N: 3.9(3.6) | $^1H$: 6.9(1H), 7.1(1H), 7.8(1H), 8.0 (2H), 8.2(1H) $^{19}F$: –63.0(1F), –63.4(1F) |
| 1-f | C: 50.4(50.5) H: 2.5(2.7) N: 4.9(4.9) | $^1H$: 6.9(1H), 7.1(2H), 7.6(1H), 7.8 (1H), 7.9(1H), 8.1(1H) $^{19}F$: –62.4 |
| 1-g | C: 55.9(56.3) H: 3.0(3.2) N: 5.9(6.0) | $^1H$: 6.4(1H), 6.7(1H), 7.0(1H), 7.6 (1H), 7.7(2H), 7.9(1H) $^{19}F$: –112.6(ddd) |
| 1-h | C: 51.0(45.2) H: 2.1(2.3) N: 4.9(4.2) | $^1H$: 6.8(1H), 6.95(1H), 7.05(1H), 7.7 (1H), 8.0(1H), 8.9(1H) $^{19}F$: –63.3 |
| 1-i | C: 49.4(49.3) H: 2.9(2.8) N: 4.4(4.4) | $^1H$: 3.6(3H), 6.3(1H), 6.6(1H), 7.7 (2H), 7.85(1H), 7.95(1H) $^{19}F$: –63.2 |
| 1-j | C: 47.4(47.4) H: 2.0(2.3) N: 4.6(4.7) | $^1H$: 6.7(m), 7.1(m), 7.5(m), 7.6(m), 7.7(m), 8.0(m), 8.2(m) $^{19}F$: 8 s resonances(–63.0—63.6) and 8 ddd resonances(–92.2—125.5) |
| 1-k | C: 43.5(44.0) H: 1.8(2.1) N: 8.5(8.4) | $^1H$: 6.9(1H), 7.15(1H), 8.1(1H), 8.3 (1H), 8.45(1H), 8.6(1H) $^{19}F$: –62.9 |
| 1-l | C: 42.2(42.1) H: 16.(1.8) N: 3.8(3.7) | $^1H$: 6.5(1H), 6.7(1H), 7.75(1H), 7.85 (1H), 8.0(1H), 8.1(1H) $^{19}F$: –58.1(1F), –63.4(1F) |

Example 3

This example illustrates the preparation of iridium complexes of the Second Formula $IrL^a L^b L^c{}_x L'{}_y L''{}_z$ above, Compound 1-n A mixture of $IrCl_3 \cdot nH_2O$ (54% Ir; 510 mg), 2-(3-trifluoromethylphenyl)quinoline (1.80 g), and silver trifluoroacetate (1.10 g) was vigorously stirred at 190–195° C. for 4 hours. The resulting solid was chromatographed on silica with dichloromethane to produce a mixture of the dicyclometalated complex and the unreacted ligand. The latter was removed from the mixture by extraction with warm hexanes. After the extracts became colorless the hexane-insoluble solid was collected and dried under vacuum. The yield was 0.29 g. $^{19}$F NMR: −63.5 (s, 6F), −76.5 (s, 3F). The structure of this complex was established by a single crystal X ray diffraction study.

Compound 1-o

A mixture of $IrCl_3.nH_2O$ (54% Ir; 500 mg), 2-(2-fluorophenyl)-3-chloro-5-trifluoromethylpyridne (2.22 g), water (0.3 mL), and silver trifluoroacetate (1.00 g) was stirred at 190° C. for 1.5 hours. The solid product was chromatographed on silica with dichloromethane to produce 0.33 g of a 2:1 co-crystallized adduct of the dicyclometalated aqua trifluoroacetato complex, compound 1-p, and the unreacted ligand. $^{19}$F NMR: −63.0 (9F), −76.5 (3F), −87.7 (2F), −114.4 (1F). The co-crystallized phenylpyridine ligand was removed by recrystallization from dichloromethane-hexanes. The structures of both the adduct and the complex were established by a single crystal X-ray diffraction study.

Example 4

This example illustrates the preparation of an hydroxo iridium dimer, having structure (VIII) above.

A mixture of $IrCl_3.nH_2O$ (54% Ir; 510 mg), 2-(4-fluorophenyl)-5-trifluoromethylpyridine (725 mg), water (5 mL), and 2-ethoxyethanol (20 mL) was vigorously stirred under reflux for 4.5 hours. After a solution of NaOH (2.3 g) in water (5 mL) was added, followed by 20 mL of water, the mixture was stirred under reflux for 2 hours. The mixture was cooled down to room temperature, diluted with 50 mL of water, and filtered. The solid was vigorously stirred under reflux with 30 mL of 1,2-dichloroethane and aqueous NaOH (2.2 g in 8 mL of water) for 6 hours. The organic solvent was evaporated from the mixture to leave a suspension of an orange solid in the aqueous phase. The orange solid was separated by filtration, thoroughly washed with water, and dried under vacuum to produce 0.94 g (95%) of the iridium hydroxo dimer (spectroscopically pure). $^1$H NMR ($CD_2Cl_2$): −1.0 (s, 1H, IrOH), 5.5 (dd, 2H), 6.6 (dt, 2H), 7.7 (dd, 2H), 7.9 (dd, 2H), 8.0 (d, 2H), 9.1 (d, 2H). $^{19}$F NMR ($CD_2Cl_2$): −62.5 (s, 3F), −109.0 (ddd, 1F).

Example 5

This example illustrates the preparation of bis-cyclometalated complexes from an iridium dimer.

Compound 1-p

A mixture of the iridium hydroxo dimer (100 mg) from Example 4, ethyl acetoacetate (0.075 mL; 4-fold excess), and dichloromethane (4 mL) was stirred at room temperature overnight. The solution was filtered through a short silica plug and evaporated to give an orange-yellow solid which was washed with hexanes and dried. The yield of the complex was 109 mg (94%). $^1$H NMR ($CD_2Cl_2$): 1.1 (t, $CH_3$), 3.9 (dm, $CH_2$), 4.8 (s, $CH_3COCH$), 5.9 (m), 6.7 (m), 7.7 (m), 8.0 (m), 8.8 (d). $^{19}$F NMR ($CD_2Cl_2$): −63.1 (s, 3F), −63.2 (s, 3F), −109.1 (ddd, 1F), −109.5 (ddd).

Analysis: Calcd: C, 44.9; H, 2.6; N, 3.5. Found: C, 44.4; H, 2.6; N, 3.3.

Compound 1-w

A solution of hydroxo iridium dimer from Example 4 (0.20 g) in THF (6 mL) was treated with 50 mg of trifluoroacetic acid, filtered through a short silica plug, evaporated to ca. 0.5 mL, treated with hexanes (8 mL), and left overnight. The yellow crystalline solid was separated, washed with hexanes, and dried under vacuum. Yield (1:1 THF solvate): 0.24 g (96%). $^{19}$F NMR ($CD_2Cl_2$, 20° C.), δ: −63.2 (s, 3F), −76.4 (s, 3F), −107.3 (ddd, 1F). $^1$H NMR ($CD_2Cl_2$, 20° C.), δ: 9.2 (br s, 1H), 8.2 (dd,1H), 8.1 (d, 1H), 7.7 (m, 1H), 6.7 (m,1H), 5.8 (dd, 1H), 3.7 (m, 2H, THF), 1.8 (m, 2H, THF).

Compound 1-x

A mixture of the trifluoroacetate intermediate, compound 1-w (75 mg), and 2-(4-bromophenyl)-5-bromopyridine (130 mg) was stirred under $N_2$ at 150–155° C. for 30 min. The resulting solid was cooled to room temperature and dissolved in $CH_2Cl_2$. The resulting solution was filtered through silica gel and evaporated. The residue was washed several times with warm hexanes and dried under vacuum to leave a yellow, yellow-photoluminescent solid. Yield: 74 mg (86%). $^{19}$F NMR ($CD_2Cl_2$, 20° C.), δ: −63.1 (s, 3F), −63.3 (s, 3F), −108.8 (ddd, 1F), −109.1 (ddd, 1F). $^1$H NMR ($CD_2Cl_2$, 20° C.), δ: 8.2 (s), 7.9 (m), 7.7 (m), 7.0 (d), 6.7 (m), 6.2 (dd), 6.0 (dd). The complex was meridional, with the nitrogens of the fluorinated ligands being trans, as confirmed by X-ray analysis.

Example 6

This example illustrates the preparation of iridium compounds of the Fifth Formula mer-Ir($L^a$)$_3$ above.

Compound 1-s

This complex was synthesized in a manner similar to compound 1-n. According to the NMR, TLC, and TGA data, the result was an approximately 1:1 mixture of the facial and meridional isomers.

Compound 1-t

A mixture of $IrCl_3.nH_2O$ (54% Ir; 0.40 g), 2-(3, 5-difluorophenyl)-5-trifluoromethylpyridine (1.40 g), AgO-$COCF_3$ (0.81 g), and water (0.5 mL) was vigorously stirred under a flow of $N_2$ as the temperature was slowly (30–40 min) brought up to 165° C. (oil bath). After 40 min at 165° C. the mixture solidified. The mixture was cooled down to room temperature. The solids were extracted with dichloromethane until the extracts decolorized. The combined dichloromethane solutions were filtered through a short silica column and evaporated. The residue was thoroughly washed with hexanes and dried under vacuum. Yield: 0.53 g (49%). $^{19}$F NMR ($CD_2Cl_2$, 20° C.), δ: −63.55 (s, 3F), −63.57 (s, 3F), −63.67 (s, 3F), −89.1 (t, 1F), −100.6 (t, 1F), −102.8 (dd, 1F), −118.6 (ddd, 1F), −119.3 (ddd, 1F), −123.3 (ddd, 1F). $^1$H NMR ($CD_2Cl_2$, 20° C.), δ: 8.4 (s), 8.1 (m), 7.9 (m), 7.6 (s), 7.5 (m), 6.6 (m), 6.4 (m). The complex was meridional, as was also confirmed by X-ray analysis.

Compound 1-u

This complex was prepared and isolated similarly to compound 1-q, then purified by crystallization from 1,2-dichloroethane—hexanes. The yield of the purified product was 53%. The complex is mer, as follows from the NMR data. $^{19}$F NMR ($CD_2Cl_2$, 20° C.), δ: −63.48 (s, 3F), −63.52 (s, 6F), −105.5 (ddd, 1F), −105.9 (ddd, 1F), −106.1 (ddd, 1F), −107.4 (t, 1F), −107.9 (t, 1F), −109.3 (t, 1F). $^1$H NMR ($CD_2Cl_2$, 20° C.), δ: 8.6 (m), 8.3 (s), 8.2 (s), 8.1 (m), 7.9 (m), 7.6 (m), 6.6 (m), 6.4 (m), 6.0 (m), 5.8 (m).

Compound 1-v

This mer-complex was prepared in a manner similar to compound 1-w, using the trifluoroacetate dicyclometalated intermediate, compound 1-x, and 2-(4-fluorophenyl)-5-trifluoromethylpyridine. $^{19}$F NMR ($CD_2Cl_2$, 20° C.), δ: −63.30 (s, 3F), −63.34 (s, 3F), −63.37 (s, 3F), −108.9 (ddd, 1F), −109.0 (ddd, 1F), −109.7 (ddd, 1F). $^1$H NMR ($CD_2Cl_2$, 20° C.), δ: 8.3–7.6 (m), 6.7 (m), 6.6 (dd), 6.3 (dd), 6.0 (dd).

This yellow-luminescent merisional complex isomerised to the green luminescent facial isomer, compound 1-b, upon sublimation at 1 atm.

Example 7

This example illustrates the formation of OLEDs using the iridium complexes of the invention.

Thin film OLED devices including a hole transport layer (HT layer), electroluminescent layer (EL layer) and at least one electron transport layer (ET layer) were fabricated by the thermal evaporation technique. An Edward Auto 306 evaporator with oil diffusion pump was used. The base vacuum for all of the thin film deposition was in the range of $10^{-6}$ torr. The deposition chamber was capable of depositing five different films without the need to break up the vacuum.

An indium tin oxide (ITO) coated glass substrate was used, having an ITO layer of about 1000–2000 Å. The substrate was first patterned by etching away the unwanted ITO area with 1 N HCl solution, to form a first electrode pattern. Polyimide tape was used as the mask. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to $10^{-6}$ torr. The substrate was then further cleaned using an oxygen plasma for about 5–10 minutes. After cleaning, multiple layers of thin films were then deposited sequentially onto the substrate by thermal evaporation. Finally, patterned metal electrodes of Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

A summary of the device layers and thicknesses is given in Table 6. In all cases the anode was ITO as discussed above, and the cathode was Al having a thickness in the range of 700–760 Å. In some of the samples, a two-layer electron transport layer was used. The layer indicated first was applied adjacent to the EL layer.

TABLE 6

$Alq_3$ = tris(8-hydroxyquinolato) aluminum
DDPA = 2,9-dimethyl-4,7-diphenyl-1,10-phenanthrolinqe
$Ir(ppy)_3$ = fac-tris(2-phenylpyridine) iridium
MPMP = bis[4-(N,N-diethylamino)-2-methylphenyl](4-methylphenyl)methane

| Sample | HT layer (Thickness, Å) | EL layer (Thickness, Å) | ET layer (Thickness, Å) |
|---|---|---|---|
| Comparative | MPMP (528) | Ir(ppy)$_3$ (408) | DDPA (106) + Alq$_3$ (320) |
| 1 | MPMP (520) | Compound 1-b (499) | DDPA (125) + Alq$_3$ (365) |
| 2 | MPMP (541) | Compound 1-b (580) | DDPA (407) |
| 3 | MPMP (540) | Compound 1-e (499) | DDPA(112) + Alq$_3$ (340) |
| 4 | MPMP (525) | Compound 1-k (406) | DDPA (106) Alq$_3$ (341) |
| 5 | MPMP (570) | Compound 1-i (441) | DDPA (107) + Alq$_3$ (339) |
| 6 | MPMP (545) | Compound 1-j (462) | DDPA (111) + Alq$_3$ (319) |
| 7 | MPMP (643) | Compound 1-g (409) | DDPA (112) + Alq$_3$ (361) |
| 8 | MPMP (539) | Compound 1-f (430) | DDPA (109) + Alq$_3$ (318) |
| 9 | MPMP (547) | Compound 1-a (412) | DDPA (105) + Alq$_3$ (300) |
| 10 | MPMP (532) | Compound 1-h (457) | DDPA (108) + Alq$_3$ (306) |
| 11 | MPMP (603) | Compound 1-d (415) | DDPA (111) + Alq$_3$ (303) |
| 12 | MPMP (551) | Compound 1-c (465) | DDPA (106) + Alq$_3$ (313) |
| 13 | MPMP (520) | Compound 1-l (405) | DDPA (410) |
| 14 | MPMP (504) | Compound 1-b (400) | DDPA (393) |
| 15 | MPMP (518) | Compound 1-b (153) | DDPA (418) |
| 16 | MPMP (556) | Compound 1-m (416) | DDPA (430) |
| 17 | MPMP (520) | Compound 1-n (419) | DDPA (420) |
| 18 | MPMP (511) | Compound 1-o (412) | DDPA (413) |
| 19 | MPMP (527) | Compound 1-p (425) | DDPA (412) |
| 20 | MPMP (504) | Compound 1-q (417) | DPA (407) |
| 21 | MPMP (525) | Compound 1-t (419) | DPA (416) |
| 22 | MPMP (520) | Compound 1-u (421) | DPA (405) |

Figure 2:
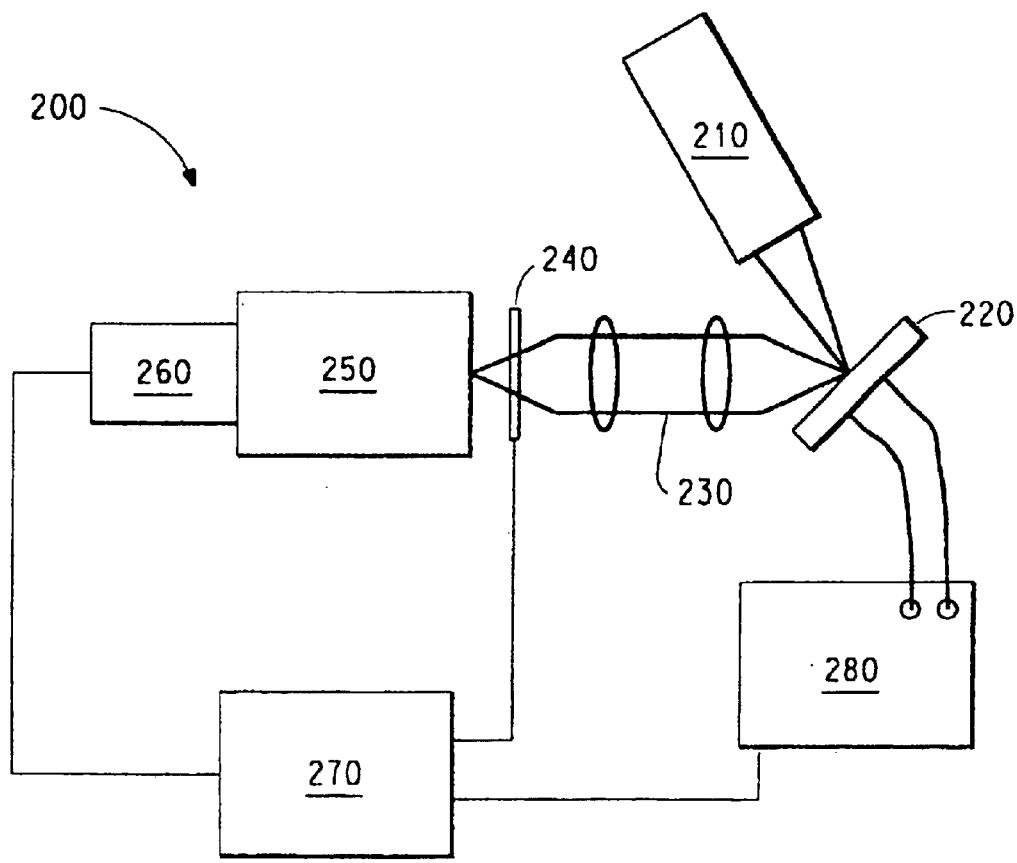
FIG. 2 is a schematic diagram of an LED testing apparatus.

The OLED samples were characterized by measuring their (1) current-voltage (I–V) curves, (2) electroluminescence radiance versus voltage, and (3) electroluminescence spectra versus voltage. The apparatus used, 200, is shown in FIG. 2. The I–V curves of an OLED sample 220, were measured with a Keithley Source-Measurement Unit Model 237, 280. The electroluminescence radiance (in the unit of Cd/m$^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in Cd/A.

The results are given in Table 7 below:

TABLE 7

Electroluminescent Properties of Iridium Compounds

| Sample | Peak Radiance, Cd/m2 | Efficiency at peak radiance, Cd/A | Peak efficiency, Cd/A | Approximate Peak Wavelengths, nm |
|---|---|---|---|---|
| Comparative | 540 at 22 V | 0.39 | 0.48 | 522 |
| 1 | 1400 at 21 V | 3.4 | 11 | 525 |
| 2 | 1900 at 25 V | 5.9 | 13 | 525 |
| 3 | 830 at 18 V | 1.7 | 13.5 | 525 |
| 4 | 7.6 at 27 V | 0.005 | 0.13 | 521 |
| 5 | 175 at 25 V | 0.27 | 1.8 | 530, 563 |
| 6 | 514 at 20 V | 1.5 | 2.2 | 560 |
| 7 | 800 at 26 V | 0.57 | 1.9 | 514 |
| 8 | 1200 at 28 V | 0.61 | 2 | 517 |
| 9 | 400 at 18 V | 1.1 | 4 | 545 |
| 10 | 190 at 16 V | 2.3 | 3.3 | 575 |
| 11 | 1150 at 25 V | 1.2 | 3.8 | 506, 526 |
| 12 | 340 at 20 V | 0.49 | 2.1 | 525 |
| 13 | 400 at 21 V | 3 | 5 | 520 |
| 14 | 1900 | 5 | 9 | 525 |
| 15 | 2500 | 6 | 11 | 525 |
| 16 | 100 at 27 V | 0.17 | 0.2 | 560 |
| 17 | 3.5 at 28 V | 0.005 | 0.014 | 575 |
| 18 | 30 at 26 V | 0.08 | 0.16 | 590 |
| 19 | 2000 at 21 V | 6 | 8 | 532 |
| 20 | 350 at 26 V | 0.60 | 1.6 | 595 |
| 21 | 1200 at 22 V |  | 5 | 545 |
| 22 | 80 at 19 V |  | 1 | 540 |

The peak efficiency is the best indication of the value of the electroluminescent compound in a device. It gives a measure of how many electrons have to be input into a device in order to get a certain number of photons out (radiance). It is a fundamentally important number, which reflects the intrinsic efficiency of the light-emitting material. It is also important for practical applications, since higher efficiency means that fewer electrons are needed in order to achieve the same radiance, which in turn means lower power consumption. Higher efficiency devices also tend to have longer lifetimes, since a higher proportion of injected electrons are converted to photons, instead of generating heat or causing an undesirable chemical side reactions. Most of the iridium complexes of the invention have much higher peak efficiencies than the parent fac-tris(2-phenylpyridine) iridium complex. Those complexes with lower efficiencies may also find utility as phosphorescent or photoluminescent materials, or as catalysts, as discussed above.

Example 8

This example illustrates the preparation of the ligand parent compound, 1-(2,4-difluoro-phenyl)-isoquinoline, having Formula XI.

2,4-difluorophenylboronic acid (Aldrich Chemical Co., 13.8 g, 87.4 mmol), 1-chloroisoquinoline (Adrich Chemical Co., 13 g, 79.4 mmol), tetrakistriphenylphosphine palladium (0) (Aldrich, 3.00 g, 2.59 mmol), potassium carbonate (EM Science, 24.2 g, 175 mmol), water (300 mL), and dimethoxyethane (Aldrich, 300 mL) were allowed to stir at reflux for 20 h under $N_2$, after which time the mixture was cooled to room temperature and the organic and aqueous layers were separated. The aqueous layer was extracted with 3×150 mL of diethyl ether, and the combined organic fractions were dried with sodium sulfate, filtered, and the filtrate was evaporated to dryness. The crude material was chromatographed on a silica gel column, first by eluting the catalyst byproduct with 4:1 hexanes/$CH_2Cl_2$, and finally the product was eluted with $CH_2Cl_2$/MeOH (9.5:0.5, product $R_f$=0.7). The pure product fractions were collected and dried in vacuo, to afford 17.7 g (92% isolated yield) of a light yellow solid, >95% pure NMR spectroscopy. $^1$H NMR ($CDCl_3$, 296 K, 300 MHz): δ 8.61 (1H, d, J=5.7 Hz), 7.89 (1H, d, J=8.2 Hz), 7.67–7.85 (3H, m), 7.52–7.63 (2H, m), 6.95–7.12 (2H, m) ppm. $^{19}$F NMR ($CDCl_3$, 296K, 282 MHz) δ −109.01 (1F, brs), −109.87 (1F, d, $J_{F\text{-}F}$=8.5 Hz).

Example 9

This example illustrates the preparation of the bridged dichloro dimer, [IrCl{2-(2,4-difluoro-phenyl)-isoquinoline}$_2$]$_2$.

1-(2,4-difluoro-phenyl)-isoquinoline from Example 8 (1.00 g, 4.15 mmol), $IrCl_3(H_2O)_3$ (Strem Chemicals, 703 mg, 1.98 mmol), and 2-ethoxyethanol (Aldrich Chemical Co., 25 mL) were allowed to stir at reflux for 15 h, after which time the precipitate was isolated by filtration, washed with methanol, and allowed to dry in vacuo, to afford 1.04 g (74%) of the product as red-orange solid, >95% pure by NMR spectroscopy. $^1$H NMR ($CD_2Cl_2$, 296 K, 300 MHz): δ8.85 (2H, d, J=6.4 Hz), 8.38 (2H, dd, J=8.8 and 9.5 Hz), 7.82–7.97 (m, 4H), 7.67–7.7.8 (2H, m), 6.81 (2H, d, J=6.4 Hz), 6.42 (2H, ddd, J=2.4, 3.3, and 11.4 Hz), 5.25 (2H, dd, J=2.4 and 8.8 Hz) ppm. $^{19}$F NMR ($CDCl_3$, 296K, 282 MHz) δ −95.7(2F, d, $J_{F\text{-}F}$=12 Hz), −108.03 (2F, d, $J_{F\text{-}F}$=12 Hz).

Example 10

This example illustrates the preparation of the bis-cyclometallated iridium complex, [Ir(acac){1-(2,4-difluoro-phenyl)-isoquinoline}$_2$], complex 8-r in Table 8.

[IrCl{1-(2,4-difluoro-phenyl)-isoquinoline}$_2$]$_2$ from Example 9 (300 mg, 0.212 mmol), sodium acetylacetonate (Aldrich Chemical Co., 78 mg, 0.636 mmol), and 2-ethoxyethanol (10 mL) were allowed to stir at 120° C. for 0.5 h. The volatile components were then removed in vacuo. The residue was taken up in dichloromethane, and this solution was passed through a pad of silica gel with dichloromethane as the eluting solvent. The resulting red-orange filtrate was evaporated to dryness, and then suspended in methanol. The precipitated product was isolated by filtration and dried in vacuo. Isolated yield=230 mg (70%). $^1$H NMR ($CD_2Cl_2$, 296 K, 300 MHz): δ 8.40 (2H. dd, I=8.8 and 9 Hz), 7.97 (2H, d, J=8.1 Hz), 7.78 (2H, ddd, J=0.7, 6.6, and 7.8 Hz), 7.70 (2H, dd, J=1.3 and 8.4 Hz), 7.66 (2H, d, J=6.4 Hz), 6.44 (2H, ddd, J=2.4, 5.9, and 5 10.8 ppm), 5.68 (2H, dd, J=2.4 and 8.5 Hz), 5.30 (1H, s), 1.78 (6H, s). $^{19}$F NMR (CDCl$_3$, 296K, 282 MHz) δ -96.15 (2F, d, JF-F=11.3 Hz), -109.13 (2F, d, J$_{F-F}$=11.3 Hz).

Compounds 8-a through 8-k, and compound 8-s in Table 8 were prepared using a similar procedure.

Compounds 8-l through 8-q in Table 8 were prepared using the procedure of Example 2.

Example 11

Thin film OLED devices were fabricated using the procedure according to Example 7. A summary of the device layers and thicknesses is given in Table 10. In all cases the anode was ITO as discussed above, and the cathode was Al having a thickness in the range of 700–760 Å.

TABLE 10

MPMP = bis[4-(N,N-diethylamino)-2-methylphenyl](4-methylphenyl)-methane
DPA = 4,7-diphenyl-1,10-phenanthroline

| Sample | HT layer (Thickness, Å) | EL layer (Thickness, Å) | ET layer (Thickness, Å) |
|---|---|---|---|
| 11-1 | MPMP (572) | Compound 8-a (419) | DPA (400) |
| 11-2 | MPMP (512) | Compound 8-b (407) | DPA (394) |
| 11-3 | MPMP (548) | Compound 8-c (441) | DPA (408) |
| 11-4 | MPMP (508) | Compound 8-d (410) | DPA (408) |
| 11-5 | MPMP (560) | Compound 8-e (421) | DPA (407) |
| 11-6 | MPMP (526) | Compound 8-f (409) | DPA (405) |
| 11-7 | MPMP (890) | Compound 8-g (408) | DPA (402) |
| 11-8 | MPMP (514) | Compound 8-h (465) | DPA (403) |
| 11-9 | MPMP (564) | Compound 8-i (418) | DPA (413) |
| 11-10 | MPMP (564) | Compound 8-j (405) | DPA (407) |
| 11-11 | MPMP (522) | Compound 8-k (400) | DPA (408) |
| 11-12 | MPMP (529) | Compound 8-l (421) | DPA (408) |
| 11-13 | MPMP (530) | Compound 8-m (411) | DPA (411) |
| 11-14 | MPMP (537) | Compound 8-o (412) | DPA (409) |
| 11-15 | MPMP (509) | Compound 8-p (405) | DPA (405) |
| 11-16 | MPMP (512) | Compound 8-q (414) | DPA (402) |
| 11-17 | MPMP (529) | Compound 8-r (442) | DPA (412) |
| 11-18 102961-31 | MPMP (524) | Compound 8-s (407) | DPA (408) |

The OLED samples were characterized as in Example 7, and the results are given in Table 12 below.

TABLE 11

Electroluminescent Properties of Iridium Compounds

| Sample | Peak Radiance, Cd/m2 | Peak efficiency, Cd/A | Approximate Peak Wavelengths, nm |
|---|---|---|---|
| 11-1 | 45 at 22 V | 0.13 | 628 |
| 11-2 | 32 at 20 V | 0.12 | >600 |
| 11-3 | 340 at 24 | 2.5 | 590 |
| 11-4 | 350 at 22 V | 1.7 | 625 |
| 11-5 | 300 at 21 V | 1.5 | >600 |
| 11-6 | 200 at 20 V | 1.1 | 605, 650 |
| 11-7 | 300 at 23 V | 5 | 605 |
| 11-8 | 280 at 21 V | 2.9 | 590 |
| 11-9 | 1000 at 20 V | 3.5 | 592 |
| 11-10 | 380 at 21 V | 2.3 | 610, 650 |
| 11-11 | 8 at 23 V | 0.25 | 624 |
| 11-12 | 800 at 20 V | 2.3 | 610, 650 |
| 11-13 | 360 at 22 V | 1.5 | 590 |
| 11-14 | 160 at 24 V | 1.2 | 590 |
| 11-15 | 80 at 21 V | 1.1 | 597 |
| 11-16 | 170 at 21 V | 0.8 | 615 |
| 11-17 | 1300 at 22 V | 4 | 600 |
| 11-18 | 540 at 20 V | 1.6 | 622 |

Example 12

This example illustrates the preparation of additional phenylpyridine ligands.

The phenylpyridine compounds 12-a through 12-j, shown in Table 12 below, were prepared as described in Example 1.

TABLE 12

| Compound | A | R$_1$ | R$_2$ | R$_3$ | R$_4$ | R$_5$ | R$_6$ | R$_7$ | R$_8$ | R$_9$ |
|---|---|---|---|---|---|---|---|---|---|---|
| 12-a | C | H | CH$_3$ | H | H | F | H | F | H | H |
| 12-b | C | H | CH$_3$ | H | H | H | CF$_3$ | H | CF$_3$ | H |
| 12-c | C | H | H | CH$_3$ | H | F | H | F | H | H |
| 12-d | C | H | CH$_3$ | H | H | H | CF$_3$ | H | H | H |
| 12-e | C | H | H | CH$_3$ | H | H | CF$_3$ | H | CF$_3$ | H |
| 12-f | C | H | H | H | H | H | CF$_3$ | H | H | H |
| 12-g | C | H | H | H | H | F | H | F | H | H |
| 12-h | C | H | t-Bu | H | H | H | H | F | H | H |
| 12-i | C | H | t-Bu | H | H | H | CF$_3$ | H | CF$_3$ | H |
| 12-j | C | H | CH$_3$ | H | H | H | H | CF$_3$ | H | H |

The analytical and NMR data are given in Table 13 below.

TABLE 13

| Compound | Yield (%) | B.p./ mm Hg (m.p.) °C. | NB No | $^1$H NMR | $^{19}$F NMR |
|---|---|---|---|---|---|
| 12-a | 61.5 | 70–72/0.03 | 101394–104 | 2.39(3H), 6.99(2H), 7.02(1H), | -102.96 (1F, m), -113.18 |

TABLE 13-continued

| Compound | Yield (%) | B.p./ mm Hg (m.p.) °C. | NB No | $^1$H NMR | $^{19}$F NMR |
|---|---|---|---|---|---|
| | | | | 7.57(1H), 7.99(1H) 8.56(1H) | (1F,m) |
| 12-b | 39 | 66–68/0.01 | 101394–115 | 2.47(3H), 7.17(1H), 7.63(1H), 7.91(1H), 8.48(2H), 8.60(1H), 9.00(1H) | −63.23 (s) |
| 12-c | 76 | 75–76/0.01 (54–56) | 101394–121 | 2.25(3H), 6.90(2H), 7.55(2H), 8.50(1H), 8.85(1H) | −110.37 (1F, m) −113.50 (1F,m) |
| 12-d | 76 | 69–70/0.06 (44–46) | 101394–129 | 2.35(3H), 7.05(1H), 7.55(2H), 8.01(1H), 8.18(1H), 8.50(1H) | −63.03 (s) |
| 12-e | 84 | (83–85) | 102960–48 | 2.43(3H) 7.66(1H), 7.87(1H), 8.47(2H), 8.59(1H) | −63.18 (s) |
| 12-f | 72 | 64–65/0.026 | 99344–13 | 7.20(1H), 7.65(3H), 8.10(1H), 8.17(1H), 8.65(1H), 9.43(1H) | −63.05 (s) |
| 12-g | 36 | 62/0.01 | 101394–93 | 6.90(1H), 7.18(2H), 7.68(2H), 7.95(1H), 8.65(1H), | −109.70 (1F, m) −113.35 (1F, m) |
| 12-h | 49 | 99–101/0.26 | 102960–117 | — | — |
| 12-i | 58 | 108–109/0.1 | 103555–3 | 1.35(9H) 7.34(1H) 7.72(1H) 7.88(1H) 8.44(2H) 8.61(1H) | −63.19 |
| 12-j | 46 | 76–77/01 (52–54) | 102960–143 | 2.46(3H) 7.15(1H) 7.60(1H) 7.73(2H) 8.11(2H) 8.59(1H) | −62.86 |

2-(2',4'-dimethoxyphenyl)-5-trifluoromethylpyridine was prepared via Kumada coupling of 2-chloro-5-trifluoromethylpyridine with 2,4-dimethoxyphenylmagnesium bromide in the presence of [(dppb)PdCl$_2$] catalyst (dppb=1,4-bis(diphenylphosphino)butane).

Example 13

This example illustrates the formation of dichloro-bridged dinuclear bis-cyclometallated Ir complexes.

The Ir complexes were prepared by the reaction between IrCl$_3$.nH$_2$O and the corresponding 2-arylpyridine in aqueous 2-ethoxyethanol. The method is similar to the literatures procedure for 2-phenylpyridine (Sprouse, S.; King, K. A.; Spellane, P. J.; Watts, R. J., J. Am. Chem. Soc., 1984, 106, 6647–53; Garces, F. O.; King, K. A.; Watts, R. J., Inorg. Chem., 1988, 27, 3464–71.). A mixture of IrCl$_3$.nH$_2$O, a 2-arylpyridine (2.2–2.8 equivalents per Ir), 2-ethoxyethanol (ca. 30 mL per 1 g of IrCl$_3$.nH$_2$O), and water (ca. 5 mL per 30 mL of 2-ethoxyethanol) was vigorously stirred under reflux (N$_2$) for 4–10 hours. After cooling to room temperature, conc. HCl (3 mL per 1 g IrCl$_3$.nH$_2$O) was added, and the mixture was stirred for 30 min. The mixture was diluted with water, stirred for 1–2 hours, and filtered. The solid product was washed with water, methanol, and dried under vacuum. The yields ranged from 65 to 99%.

Example 14

This example illustrates the formation of Ir complexes of the invention having the Sixth Formula, where L" is Cl. Dicyclometalated Arylpyridine Iridium (III) Mononuclear Complexes Containing Monodentate Tertiary Phosphine, CO, or Isonitrile Ligands.

A mixture of a the dichloro-bridged dinuclear bis-cyclometallated Ir complex made as in Example 13, a monodentate ligand L', and 1,2-dichloroethane (DCE) or toluene was stirred under reflux (N$_2$ or CO when L' is CO) until all solids dissolved and then for additional 3 min –1 h. The products were isolated and purified by evaporation and crystallization in air. Detailed procedures for selected complexes are given below. All complexes were characterized by NMR spectroscopic data ($^{31}$P NMR=$^{31}$P-{$^1$H} NMR). Satisfactory combustion analyses were not obtained due to insufficient thermal stability of the complexes. Both isomers of compound 9-k, the major isomer with the nitrogens trans and the minor isomer with the nitrogens cis, were characterized by single-crystal X-ray diffraction.

Complex 9-d (Table 9).

A mixture of the dichloro-bridged dinuclear bis-cyclometallated Ir complex made with phenylpyridine compound 12-f from Example 12 (100 mg); ligand NC-1, which is 2,6-(CH$_3$)$_2$C$_6$H$_3$NC, (26 mg) as ligand L' (purchased from the Fluka line of chemicals, from Sigma-Aldrich); and DCE (1.5 mL) was stirred under reflux for 5 min. Upon cooling to room temperature the strongly bluish-green photoluminescent solution was treated with hexanes (15 mL, portionwise). The yellow crystals were separated, washed with hexanes (3×3 mL), and dried under vacuum. Yield: 0.115 g (96%). $^1$H NMR (CD$_2$Cl$_2$, 20° C.), δ: 2.2 (s, 6H, CH$_3$); 6.35 (d, 1H, arom H); 6.65 (d, 1H, arom H); 7.1 (m, 4H, arom H); 7.3 (m, 1H, arom H); 7.5 (m, 1H, arom H); 7.9 (d, 2H, arom H); 8.1 (m, 5H, arom H); 9.4 (d, 1H, arom H); 10.0 (d, 1H, arom H). $^{19}$F NMR (CD$_2$Cl$_2$, 20° C.), δ: −62.7 (s, 3F, CF$_3$); −62.8 (s, 3F, CF$_3$).

Complex 9-g (Table 9):

A mixture of the dichloro-bridged dinuclear bis-cyclometallated Ir complex made with phenylpyridine compound 2-y from Example 1 (120 mg), ligand NC-1, which is 2,6-(CH$_3$)$_2$C$_6$H$_3$NC, (26 mg) as ligand L' (purchased from the Fluka line of chemicals, from Sigma-Aldrich); and DCE (2 mL) was stirred under reflux for 10 min. Upon cooling to room temperature the strongly bluish-green photoluminescent solution was treated with hexanes (4 mL, portionwise). The yellow crystals were separated, washed with hexanes (3×3 mL), and dried under vacuum. Yield: 0.13 g (93%). $^1$H NMR (CD$_2$Cl$_2$, 20° C.), δ: 2.2 (s, 6H, CH$_3$); 6.35 (d, 1H, arom H); 6.65 (d, 1H, arom H); 7.1 (m, 5H, arom H); 8.0 (d, 2H, arom H); 8.25 (m, 4H, arom H); 9.6 (s, 1H, arom H); 10.4 (s, 1H, arom H). $^{19}$F NMR (CD$_2$Cl$_2$, 20° C.), δ: −62.8 (s, 6F, CF$_3$); −62.9 (s, 3F, CF$_3$); −63.0 (s, 3F, CF$_3$).

Complex 9-i (Table 9)

A mixture of the dichloro-bridged dinuclear bis-cyclometallated Ir complex made with phenylpyridine compound 2-k from Example 1 (300 mg), triphenylphosphine (120 mg) as ligand L'; and toluene (6 mL) was stirred under reflux for 10 min. Upon cooling to room temperature yellow crystals precipitated from the green photoluminescent solution. After 2 days at room temperature, hexanes (8 mL) was added. After 1 day, the yellow crystals were separated, washed with hexanes (3×3 mL), and dried under vacuum. Yield: 0.41 g (97%). $^1$H NMR (CD$_2$Cl$_2$, 20° C.), δ: 5.5 (m, 2H, arom H); 6.7 (m, 2H, arom H); 7.2–7.9 (m, 21H, arom H); 8.05 (s, 2H, arom H); 9.15 (s, 1H, arom H); 9.65 (s, 1H, arom H). $^{19}$F NMR (CD$_2$Cl$_2$, 20° C.), δ: −62.9 (s, 3F, CF$_3$); −63.0 (s, 3F, CF$_3$); −107.9 (m, 1F, arom F); −108.3 (m, 1F, arom F). $^{31}$P NMR (CD$_2$Cl$_2$, 20° C.), δ: −3.2 (d, J$_{P-F}$=5.9 Hz). The product contains a minor isomer (ca. 10%) with the following NMR parameters: $^{19}$F NMR (CD$_2$Cl$_2$, 20° C.), δ: −63.5 (s, 3F, CF$_3$); −63.9 (s, 3F, CF$_3$); −107.4 (m, 1F, arom F); −108.9 (m, 1F, arom F). $^{31}$P NMR (CD$_2$Cl$_2$, 20° C.), δ: −10.8 (d, J$_{P-F}$=6.3 Hz).

Complex 9-k (Table 9)

A mixture of the dichloro-bridged dinuclear bis-cyclometallated Ir complex made with phenylpyridine compound 2-k from Example 1 (102 mg); the triarylphosphine compound (Ar$_f$)$_3$P, where Ar$_f$=3,5-(CF$_3$)$_2$C$_6$H$_3$ (102 mg) as ligand L'; and toluene (8 mL) was stirred under reflux for 10 min until all solids dissolved. After cooling to room temperature the mixture was treated with hexanes (10 mL), and kept at ca. +10° C. for 3 h. The yellow crystalline solid was separated, washed with hexanes, and dried under vacuum. The compound exhibited sky-blue photoluminescence. $^{19}$F NMR analysis of this product indicated ca. 10% of unreacted dichloro bridged complex. After heating the solid in boiling toluene in the presence of L$_5$ (30 mg) and then cooling at ca. +10° C. for 12 hours, complex 9-k was isolated, free of any dichloro gridged complex. It was washed with hexanes, and dried under vacuum. Yield: 0.17 g (86%). $^1$H NMR (CD$_2$Cl$_2$, 20° C.), δ: 5.4 (m, 1H, arom H); 5.9 (m, 1H, arom H); 6.75 (m, 2H, arom H); 7.2 (m, 2H, arom H); 7.75 (m, 2H, arom H); 7.9 (m, 7H; arom H); 8.05 (s, 2H, arom H); 8.15 (s, 2H, arom H); 8.85 (s, 1H, arom H); 9.4 (s, 1H, arom H). $^{19}$F NMR (CD$_2$Cl$_2$, 20° C.), δ: −63.2 (s, 3F, CF$_3$); −63.9 (s, 3F, CF$_3$); −64.0 (s, 18F, L$_5$ CF$_3$); −105.4 (m, 1F, arom F); −106.1 (m, 1F, arom F). $^{31}$P NMR (CD$_2$Cl$_2$, 20° C.), δ: −2.2 (d, J$_{P-F}$=5.9 Hz). This complex has the nitrogen atoms trans to each other (X-ray). In the crop of single crystals submitted for X-ray analysis a few crystals of different shape were also found. One of those few was also analyzed by X-ray diffraction, which established cis-arrangement of the N atoms around Ir for the minor isomer.

Complex 9-I (Table 9)

Carbon monoxide, as L', was bubbled through a boiling solution of the dichloro-bridged dinuclear bis-cyclometallated Ir complex made with phenylpyridine compound 2-k from Example 1 (180 mg) in DCE (8 mL). The heater was turned off and the solution was allowed to cool slowly to room temperature with CO bubbling through the mixture. When pale-yellow crystals began to precipitate hexanes (10 mL) was added slowly, in 2-mL portions. After 30 min at room temperature the crystals (whitish-blue photoluminescent) were separated, washed with hexanes, and dried under vacuum for 15 min. Yield: 0.145 g (78%). $^1$H NMR (CD$_2$Cl$_2$, 20° C.), δ: 5.6 (m, 1H, arom H); 6.15 (m, 1H, arom H); 6.8 (m, 2H, arom H); 7.8 (m, 2H, arom H); 8.1 (m, 2H, arom H); 8.25 (m, 2H, arom H); 9.2 (s, 1H, arom H); 10.15 (s, 1H, arom H). $^{19}$F NMR (CD$_2$Cl$_2$, 20° C.), δ: −62.8 (s, 3F, CF$_3$); -62.9 (s, 3F, CF$_3$); −106.5 (m, 1F, arom F); −106.7 (m, 1F, arom F).

Complexes 9-a, 9-b, 9-c, 9-e, 9-f, 9-h, and 9-i, were made using the same procedure as for complex 9-d, using phenylpyridine compounds 12-a, 12-c, 12-g, 12-d, 2-k, 12-f, and 2-k, respectively.

Example 15

Thin film OLED devices were fabricated using the procedure according to Example 7. A summary of the device layers and thicknesses is given in Table 14. In all cases the anode was ITO as discussed above, and the cathode was Al having a thickness in the range of 700–760 Å.

TABLE 14

MPMP = bis[4-(N,N-diethylamino)-2-methylphenyl](4-methylphenyl)methane
DPA = 4,7-diphenyl-1,10-phenanthroline

| Sample | HT layer (Thickness, Å) | EL layer (Thickness, Å) | ET layer (Thickness, Å) |
|---|---|---|---|
| 15-1 | MPMP (516) | Compound 9-a (408) | DPA (413) |
| 15-2 | MPMP (518) | Compound 9-c (404) | DPA (402) |
| 15-3 | MPMP (508) | Compound 9-d (354) | DPA (421) |
| 15-4 | MPMP (504) | Compound 9-e (403) | DPA (410) |
| 15-5 102924-5 | MPMP (501) | Compound 9-f (407) | DPA (415) |
| 15-6 102924-40 | MPMP (518) | Compound 9-g (404) | DPA (405) |

The OLED samples were characterized as in Example 7, and the results are given in Table 15 below.

TABLE 15

Electroluminescent Properties of Iridium Compounds

| Sample | Peak Radiance, Cd/m2 | Peak efficiency, Cd/A | Approximate Peak Wavelengths, nm |
|---|---|---|---|
| 15-1 | 6 at 16 V | 0.7 | 450 + 500 |
| 15-2 | 1 at 21 V | 0.25 | 510 |
| 15-3 | 60 at 22 V | 0.8 | 464 + 493 |
| 15-4 | 25 at 23 V | 1.2 | 460 + 512 |
| 15-5 | 320 at 22 V | 2.4 | 538 |
| 15-6 | 350 at 23 V | 1.5 | 484 + 509 |

What is claimed is:
1. A compound having the formula:

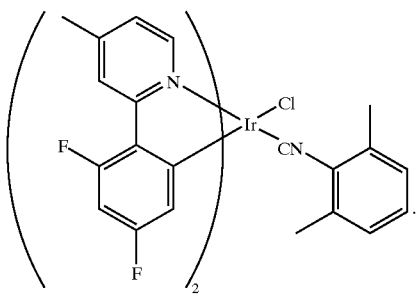

2. A compound having the formula:
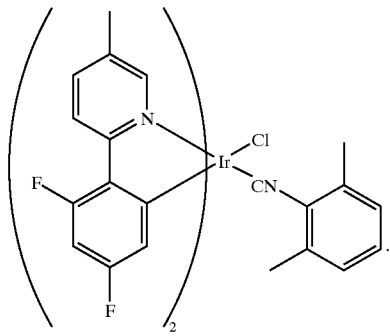
3. A compound having the formula:
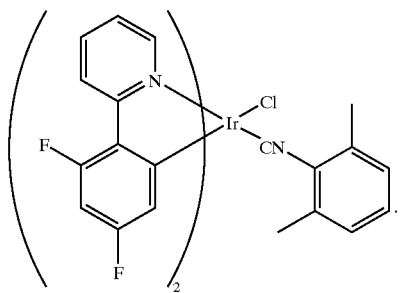
4. A compound having the formula:
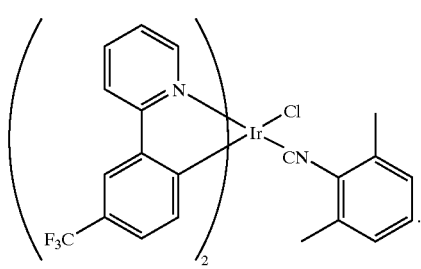
5. A compound having the formula:
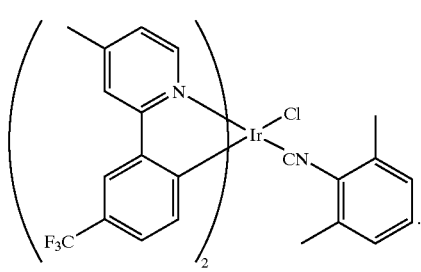
6. A compound having the formula:
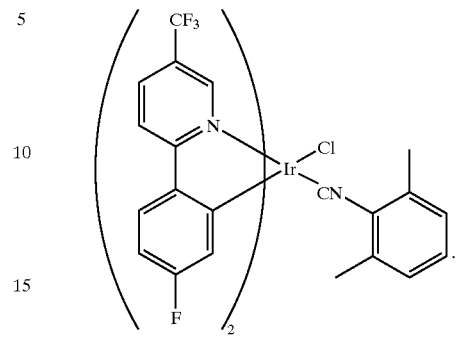
7. A compound having the formula:
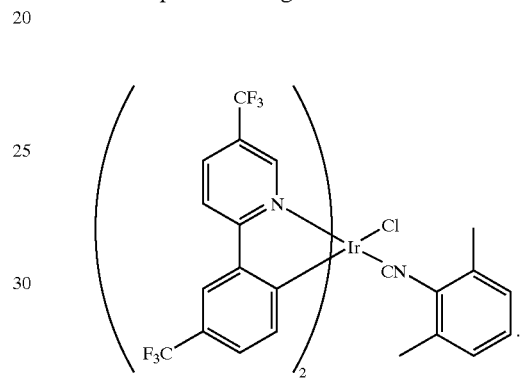
8. A compound having the formula:
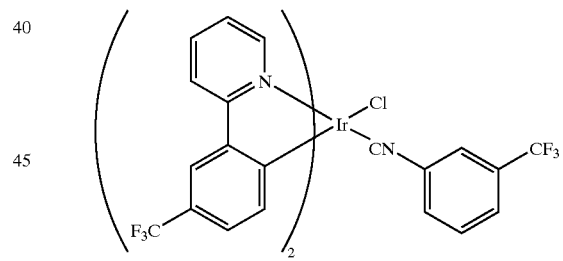
9. A compound having the formula:
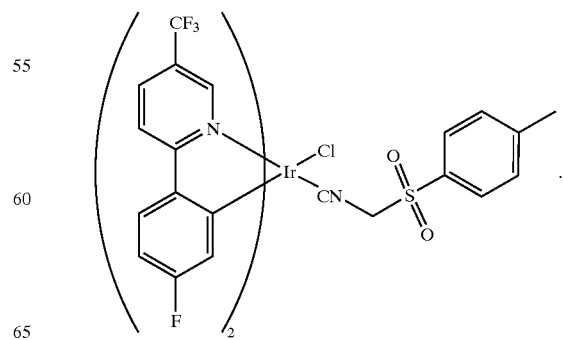

10. An electronic device comprising an organic layer comprising at least one compound having the formula set forth in claims 1 to 9.

11. An electronic device comprising a light emitting layer comprising at least one compound from claims 1 to 9.

12. An electronIc deyice comprising a charge transport layer comprising at least one compound from claims 1 to 9.

* * * * *